(12) United States Patent
Seed et al.

(10) Patent No.: US 7,399,847 B1
(45) Date of Patent: Jul. 15, 2008

(54) NUCLEIC ACIDS ENCODING ARTIFICIAL P-SELECTIN LIGANDS

(75) Inventors: Brian Seed, Boston, MA (US); Tara Pouyani, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 1826 days.

(21) Appl. No.: 08/756,018

(22) Filed: Nov. 25, 1996

(51) Int. Cl.
*C07H 21/04* (2006.01)
*C12N 1/20* (2006.01)
*C12N 15/00* (2006.01)

(52) U.S. Cl. ............... 536/23.5; 435/252.3; 435/320.1

(58) Field of Classification Search .............. 424/134.1; 530/350; 435/71.1, 252.3; 536/23.1, 23.53
See application file for complete search history.

(56) References Cited

U.S. PATENT DOCUMENTS

| | | | |
|---|---|---|---|
| 4,663,281 A | | 5/1987 | Gillies et al. |
| 5,304,640 A | | 4/1994 | Lasky et al. |
| 5,595,900 A | * | 1/1997 | Lowe et al. |
| 5,681,722 A | * | 10/1997 | Newman et al. |
| 5,723,583 A | * | 3/1998 | Seed et al. |
| 5,843,707 A | * | 12/1998 | Larsen et al. |

FOREIGN PATENT DOCUMENTS

WO 9410309 * 5/1994

OTHER PUBLICATIONS

Meier et al. Biochem J. 294: 25-30 (1993).*
Norgard et al. PNAS 90: 1068-1072 (1993).*
Aruffo et al. Cell 67: 35-44 (1991).*
McEver et al., J. Clin. Invest. 84:92-99 (1989).
Bonfanti et al., Blood 73:1109-1112 (1989).
Hsu-Lin et al., J. Biol. Chem. 259:9121-9126 (1984).
Stenberg et al., J. Cell Biol. 101:880-886 (1985).
Hattori et al., J. Biol. Chem. 264:9053-9060 (1989).
Kubes and Kanwar, J. Imunol. 152:3570-3577 (1994).
Thorlacius et al., Biochem. Biophys. Res. Communications 203:1043-1049 (1994).
Foreman et al., J. Clin. Invest. 94:1147-1155 (1994).
Patel et al., J. Cell Biol. 112:749-759 (1991).
Lehr et al., Laboratory Invest. 71:380-386 (1994).
Gebuhrer et al., Biochem. J. 306:293-298 (1995).
Larsen et al., Cell 59:305-312 (1989).
Hamburger and McEver, Blood 75:550-554 (1990).
Geng et al., Nature 343:757-760 (1990).
Gamble et al., Science 249:414-417 (1990).
Lawrence and Springer, Cell 65:859-873 (1991).
Mayadas et al., Cell 74:541-554 (1993).
Aruffo et al., EMBO J. 6:3313-3316 (1991).
Walz et al., Science 250:1131-1135 (1990).
Field et al., Mol. Cell. Biol. 8:2159-2165 (1988).
Sasaki et al., J. Biol. Chem. 269:14730-14737 (1994).
Natsuka et al., J. Biol. Chem. 269:16789-16794 (1994).
Pallant et al., Proc. Natl. Acad. Sci. 86:1328-1332 (1989).
Shelley et al., Proc. Natl. Acad. Sci. 86:2819-2823 (1989).
Lasky et al., Science 258:964-969 (1992).
Simmons et al., J. Immunol. 148:267-271 (1992).
Sako et al., Cell 75:1179-1186 (1993).
Lawrence et al., Blood 75:227-237 (1990).
Lowe et al., Cell 63:475 (1990).
Zettlemeisl et al., DNA Cell Biol. 9:347 (1990).
Board et al., Gene 44:127 (1986).
Aruffo et al., Cell 61:1303 (1990).
Libert et al., J. Exp. Med. 180:1571-1575 (1994).
Moore et al., J. Biol. Chem. 269:23318-23327 (1994).

* cited by examiner

*Primary Examiner*—G. R. Ewoldt
(74) *Attorney, Agent, or Firm*—Clark & Elbing LLP

(57) ABSTRACT

Disclosed herein are organic molecules to which are covalently bonded a sialyl-Le$^x$ determinant and a sulfated determinant, at least one of these determinants being positioned at a non-naturally occurring site on the molecule. Also disclosed are particular P-selectin ligands and P-selectin ligand-antibody fusions. These molecules, ligands, and fusion proteins find use in methods of reducing or protecting against inflammation and extravasation-dependent adverse reactions, such as organ damage and clotting (for example, associated with adult respiratory distress syndrome or ischemic myocardial injury).

6 Claims, 26 Drawing Sheets

```
    AAGCTTACCACCATGGACTGGACCTGGAGGTTCCTCTTCTTTGTGGTGGCAGCAGCTACA
  1 ---------+---------+---------+---------+---------+---------+  60
    TTCGAATGGTGGTACCTGACCTGGACCTCCAAGGAGAAGAAACACCACCGTCGTCGATGT

K  L  T  T  M  D  W  T  W  R  F  L  F  F  V  V  A  A  A  T   -

GGTGTCCAGTCCCAGGTGCAGCTGGTGCAGTCTGGGGCTGAGGTGAAGAAGCCTGGGTCC
 61 ---------+---------+---------+---------+---------+---------+ 120
    CCACAGGTCAGGGTCCACGTCGACCACGTCAGACCCCGACTCCACTTCTTCGGACCCAGG

G  V  Q  S  Q  V  Q  L  V  Q  S  G  A  E  V  K  K  P  G  S   -

TCGGTGAAGGTCTCCTGCAAGGCTTCTGGAGGCACCTTCAGCAGCTATGCTATCAGCTGG
121 ---------+---------+---------+---------+---------+---------+ 180
    AGCCACTTCCAGAGGACGTTCCGAAGACCTCCGTGGAAGTCGTCGATACGATAGTCGACC

S  V  K  V  S  C  K  A  S  G  G  T  F  S  S  Y  A  I  S  W   -

GTGCGACAGGCCCCTGGACAAGGGCTTGAGTGGATGGGAGGGATCATCCCTATCTTTGGT
181 ---------+---------+---------+---------+---------+---------+ 240
    CACGCTGTCCGGGGACCTGTTCCCGAACTCACCTACCCTCCCTAGTAGGGATAGAAACCA

V  R  Q  A  P  G  Q  G  L  E  W  M  G  G  I  I  P  I  F  G   +

ACAGCAAACTACGCACAGAAGTTCCAGGGCAGAGTCACGATTACCGCGGACGAATCCACG
241 ---------+---------+---------+---------+---------+---------+ 300
    TGTCGTTTGATGCGTGTCTTCAAGGTCCCGTCTCAGTGCTAATGGCGCCTGCTTAGGTGC

T  A  N  Y  A  Q  K  F  Q  G  R  V  T  I  T  A  D  E  S  T   -

AGCACAGCCTACATGGAGCTGAGCAGCCTGAGATCTGAGGACACGGCCGTGTATTACTGT
301 ---------+---------+---------+---------+---------+---------+ 360
    TCGTGTCGGATGTACCTCGACTCGTCGGACTCTAGACTCCTGTGCCGGCACATAATGACA

S  T  A  Y  M  E  L  S  S  L  R  S  E  D  T  A  V  Y  Y  C   -

GCGAGAGATAATGGAGCGTATTGTAGTGGTGGTAGCTGCTACTCGGGCTGGTTCGACCCC
361 ---------+---------+---------+---------+---------+---------+ 420
    CGCTCTCTATTACCTCGCATAACATCACCACCATCGACGATGAGCCCGACCAAGCTGGGG

A  R  D  N  G  A  Y  C  S  G  G  S  C  Y  S  G  W  F  D  P   -

TGGGGCCAGGGAACCCTGGTCACCGTCTCTTCAGGTGAGTACTGAATTCTAGCTTTCTGG
421 ---------+---------+---------+---------+---------+---------+ 480
    ACCCCGGTCCCTTGGGACCAGTGGCAGAGAAGTCCACTCATGACTTAAGATCGAAAGACC

```
      GGCAGGCCAGGCCTGACCTTGGCTTTGGGGCAGGGAGGGGGCTAAGGTGAGGCAGGTGGC
481   ---------+---------+---------+---------+---------+---------+ 540
      CCGTCCGGTCCGGACTGGAACCGAAACCCCGTCCCTCCCCCGATTCCACTCCGTCCACCG

GCCAGCAGGTGCACACCCAATGCCCATGAGCCCAGACACTGGACGCTGAACCTCGCGGAC
541   ---------+---------+---------+---------+---------+---------+ 600
      CGGTCGTCCACGTGTGGGTTACGGGTACTCGGGTCTGTGACCTGCGACTTGGAGCGCCTG

AGTTAAGAACCCAGGGGCCTCTGCGCCTGGGCCCAGCTCTGTCCCACACCGCGGTCACAT
601   ---------+---------+---------+---------+---------+---------+ 660
      TCAATTCTTGGGTCCCCGGAGACGCGGACCCGGGTCGAGACAGGGTGTGGCGCCAGTGTA

GGCACCACCTCTCTTGCAGCCTCCACCAAGGGCCCATCGGTCTTCCCCCTGGCACCCTCC
661   ---------+---------+---------+---------+---------+---------+ 720
      CCGTGGTGGAGAGAACGTCGGAGGTGGTTCCCGGGTAGCCAGAAGGGGGACCGTGGGAGG
                  A  S  T  K  G  P  S  V  F  P  L  A  P  S       -

TCCAAGAGCACCTCTGGGGGCACAGCGGCCCTGGGCTGCCTGGTCAAGGACTACTTCCCC
721   ---------+---------+---------+---------+---------+---------+ 780
      AGGTTCTCGTGGAGACCCCCGTGTCGCCGGGACCCGACGGACCAGTTCCTGATGAAGGGG
       S  K  S  T  S  G  G  T  A  A  L  G  C  L  V  K  D  Y  F  P -

GAACCGGTGACGGTGTCGTGGAACTCAGGCGCCCTGACCAGCGGCGTGCACACCTTCCCG
781   ---------+---------+---------+---------+---------+---------+ 840
      CTTGGCCACTGCCACAGCACCTTGAGTCCGCGGGACTGGTCGCCGCACGTGTGGAAGGGC
       E  P  V  T  V  S  W  N  S  G  A  L  T  S  G  V  H  T  F  P -

GCTGTCCTACAGTCCTCAGGACTCTACTCCCTCAGCAGCGTGGTGACCGTGCCCTCCAGC
841   ---------+---------+---------+---------+---------+---------+ 900
      CGACAGGATGTCAGGAGTCCTGAGATGAGGGAGTCGTCGCACCACTGGCACGGGAGGTCG
       A  V  L  Q  S  S  G  L  Y  S  L  S  S  V  V  T  V  P  S  S -

AGCTTGGGCACCCAGACCTACATCTGCAACGTGAATCACAAGCCCAGCAACACCAAGGTG
901   ---------+---------+---------+---------+---------+---------+ 960
      TCGAACCCGTGGGTCTGGATGTAGACGTTGCACTTAGTGTTCGGGTCGTTGTGGTTCCAC
       S  L  G  T  Q  T  Y  I  C  N  V  N  H  K  P  S  N  T  K  V -

GACAAGAAAGTTGGTGAGAGGCCAGCACAGGGAGGGAGGGTGTCTGCTGGAAGCAGGCTC
961   ---------+---------+---------+---------+---------+---------+ 1020
      CTGTTCTTTCAACCACTCTCCGGTCGTGTCCCTCCCTCCCACAGACGACCTTCGTCCGAG
       D  K  K  V
```

Fig. 10B

```
     AGCGCTCCTGCCTGGACGCATCCCGGCTATGCAGCCCCAGTCCAGGGCAGCAAGGCAGGC
1021 ---------+---------+---------+---------+---------+---------+ 1080
     TCGCGAGGACGGACCTGCGTAGGGCCGATACGTCGGGGTCAGGTCCCGTCGTTCCGTCCG

CCCGTCTGCCTCTTCACCCGGAGCCTCTGCCCGCCCCACTCATGCTCAGGGAGAGGGTCT
1081 ---------+---------+---------+---------+---------+---------+ 1140
     GGGCAGACGGAGAAGTGGGCCTCGGAGACGGGCGGGGTGAGTACGAGTCCCTCTCCCAGA

TCTGGCTTTTTCCCAGGCTCTGGGCAGGCACAGGCTAGGTGCCCCTAACCCAGGCCCTGC
1141 ---------+---------+---------+---------+---------+---------+ 1200
     AGACCGAAAAAGGGTCCGAGACCCGTCCGTGTCCGATCCACGGGGATTGGGTCCGGGACG

ACACAAAGGGGCAGGTGCTGGGCTCAGACCTGCCAAGAGCCATATCCGGGAGGACCCTGC
1201 ---------+---------+---------+---------+---------+---------+ 1260
     TGTGTTTCCCCGTCCACGACCCGAGTCTGGACGGTTCTCGGTATAGGCCCTCCTGGGACG

CCCTGACCTAAGCCCACCCCAAAGGCCAAACTCTCCACTCCCTCAGCTCGGACACCTTCT
1261 ---------+---------+---------+---------+---------+---------+ 1320
     GGGACTGGATTCGGGTGGGGTTTCCGGTTTGAGAGGTGAGGGAGTCGAGCCTGTGGAAGA

CTCCTCCCAGATTCCAGTAACTCCCAATCTTCTCTCTGCAGAGCCCAAATCTTGTGACAA
1321 ---------+---------+---------+---------+---------+---------+ 1380
     GAGGAGGGTCTAAGGTCATTGAGGGTTAGAAGAGAGACGTCTCGGGTTTAGAACACTGTT
                                        E   P   K   S   C   D   K  -

AACTCACACATGCCCACCGTGCCCAGGTAAGCCAGCCCAGGCCTCGCCCTCCAGCTCAAG
1381 ---------+---------+---------+---------+---------+---------+ 1440
     TTGAGTGTGTACGGGTGGCACGGGTCCATTCGGTCGGGTCCGGAGCGGGAGGTCGAGTTC
      T   H   T   C   P   P   C   P

GCGGGACAGGTGCCCTAGAGTAGCCTGCATCCAGGGACAGGCCCCAGCCGGGTGCTGACA
1441 ---------+---------+---------+---------+---------+---------+ 1500
     CGCCCTGTCCACGGGATCTCATCGGACGTAGGTCCCTGTCCGGGGTCGGCCCACGACTGT

CGTCCACCTCCATCTCTTCCTCAGCACCTGAACTCCTGGGGGGACCGTCAGTCTTCCTCT
1501 ---------+---------+---------+---------+---------+---------+ 1560
     GCAGGTGGAGGTAGAGAAGGAGTCGTGGACTTGAGGACCCCCCTGGCAGTCAGAAGGAGA
                            A   P   E   L   L   G   G   P   S   V   F   L   F  -
```

Fig. 10C

```
     TCCCCCCAAAACCCAAGGACACCCTCATGATCTCCCGGACCCCTGAGGTCACATGCGTGG
1561 ---------+---------+---------+---------+---------+---------+ 1620
     AGGGGGGTTTTGGGTTCCTGTGGGAGTACTAGAGGGCCTGGGGACTCCAGTGTACGCACC

P  P  K  P  K  D  T  L  M  I  S  R  T  P  E  V  T  C  V  V -

TGGTGGACGTGAGCCACGAAGACCCTGAGGTCAAGTTCAACTGGTACGTGGACGGCGTGG
1621 ---------+---------+---------+---------+---------+---------+ 1680
     ACCACCTGCACTCGGTGCTTCTGGGACTCCAGTTCAAGTTGACCATGCACCTGCCGCACC
                                          N     S
       V  D  V  S  H  E  D  P  E  V  K  F  N  W  Y  V  D  G  V  E -

AGGTGCATAATGCCAAGACAAAGCCGCGGGAGGAGCAGTACAACAGCACGTACCGGGTGG
1681 ---------+---------+---------+---------+---------+---------+ 1740
     TCCACGTATTACGGTTCTGTTTCGGCGCCCTCCTCGTCATGTTGTCGTGCATGGCCCACC
            N                             N     S
       V  H  N  A  K  T  K  P  R  E  E  Q  Y  N  S  T  Y  R  V  V -

TCAGCGTCCTCACCGTCCTGCACCAGGACTGGCTGAATGGCAAGGAGTACAAGTGCAAGG
1741 ---------+---------+---------+---------+---------+---------+ 1800
     AGTCGCAGGAGTGGCAGGACGTGGTCCTGACCGACTTACCGTTCCTCATGTTCACGTTCC
                                    N
       S  V  L  T  V  L  H  Q  D  W  L  N  G  K  E  Y  K  C  K  V -

TCTCCAACAAAGCCCTCCCAGCCCCCATCGAGAAAACCATCTCCAAAGCCAAAGGTGGGA
1801 ---------+---------+---------+---------+---------+---------+ 1860
     AGAGGTTGTTTCGGGAGGGTCGGGGGTAGCTCTTTTGGTAGAGGTTTCGGTTTCCACCCT
            N
       S  N  K  A  L  P  A  P  I  E  K  T  I  S  K  A  K

CCCGTGGGGTGCGAGGGCCACATGGACAGAGGCCGGCTCGGCCCACCCTCTGCCCTGAGA
1861 ---------+---------+---------+---------+---------+---------+ 1920
     GGGCACCCCACGCTCCCGGTGTACCTGTCTCCGGCCGAGCCGGGTGGGAGACGGGACTCT

GTGACCGCTGTACCAACCTCTGTCCTACAGGGCAGCCCCGAGAACCACAGGTGTACACCC
1921 ---------+---------+---------+---------+---------+---------+ 1980
     CACTGGCGACATGGTTGGAGACAGGATGTCCCGTCGGGGCTCTTGGTGTCCACATGTGGG

G  Q  P  R  E  P  Q  V  Y  T  L -

TGCCCCCATCCCGGGATGAGCTGACCAAGAACCAGGTCAGCCTGACCTGCCTGGTCAAAG
1981 ---------+---------+---------+---------+---------+---------+ 2040
     ACGGGGGTAGGGCCCTACTCGACTGGTTCTTGGTCCAGTCGGACTGGACGGACCAGTTTC

```
     GCTTCTATCCCAGCGACATCGCCGTGGAGTGGGAGAGCAATGGGCAGCCGGAGAACAACT
2041 ---------+---------+---------+---------+---------+---------+ 2100
     CGAAGATAGGGTCGCTGTAGCGGCACCTCACCCTCTCGTTACCCGTCGGCCTCTTGTTGA

F  Y  P  S  D  I  A  V  E  W  E  S  N  G  Q  P  E  N  N  Y -

ACAAGACCACGCCTCCCGTGCTGGACTCCGACGGCTCCTTCTTCCTCTACAGCAAGCTCA
2101 ---------+---------+---------+---------+---------+---------+ 2160
     TGTTCTGGTGCGGAGGGCACGACCTGAGGCTGCCGAGGAAGAAGGAGATGTCGTTCGAGT

K  T  T  P  P  V  L  D  S  D  G  S  F  F  L  Y  S  K  L  T -

CCGTGGACAAGAGCAGGTGGCAGCAGGGGAACGTCTTCTCATGCTCCGTGATGCATGAGG
2161 ---------+---------+---------+---------+---------+---------+ 2220
     GGCACCTGTTCTCGTCCACCGTCGTCCCCTTGCAGAAGAGTACGAGGCACTACGTACTCC

V  D  K  S  R  W  Q  Q  G  N  V  F  S  C  S  V  M  H  E  A -

CTCTGCACAACCACTACACGCAGAAGAGCCTCTCCCTGTCTCCGGGTAAATGAGTGCGAC
2221 ---------+---------+---------+---------+---------+---------+ 2280
     GAGACGTGTTGGTGATGTGCGTCTTCTCGGAGAGGGACAGAGGCCCATTTACTCACGCTG

L  H  N  H  Y  T  Q  K  S  L  S  L  S  P  G  K  *

GGCCGGC
2281 -------
     CCGGCCG
```

Fig. 10E

```
   1  ATGGCGCTGT CCTGGGTTCT TACAGTCCTG AGCCTCCTAC CTCTGCTGGA
  51  AGCCCAGATC CCATTGTGTG CCAACCTAGT ACCGGTGCCC ATCACCAACG
 101  CCACCCTGGA CCAGATCACT GGCAAGTGGT TTTATATCGC ATCGGCCTTT
 151  CGAAACGAGG AGTACAATAA GTCGGTTCAG GAGATCCAAG CAACCTTCTT
 201  TTACTTCACC CCCAACAAGA CAGAGGACAC GATCTTTCTC AGAGAGTACC
 251  AGACCCGACA GGACCAGTGC ATCTATAACA CCACCTACCT GAATGTCCAG
 301  CGGGAAAATG GGACCATCTC CAGATACGTG GGAGGCCAAG AGCATTTCGC
 351  TCACTTGCTG ATCCTCAGGG ACACCAAGAC CTACATGCTT GCTTTTGACG
 401  TGAACGATGA GAAGAACTGG GGGCTGTCTG TCTATGCTGA CAAGCCAGAG
 451  ACGACCAAGG AGCAACTGGG AGAGTTCTAC GAAGCTCTCG ACTGCTTGCG
 501  CATTCCCAAG TCAGATGTCG TGTACACCGA TTGGAAAAAG GATAAGTGTG
 551  AGCCACTGGA GAAGCAGCAC GAGAAGGAGA GGAAACAGGA GGAGGGGGAA
 601  TCGGATCCCG AGGGTGAGTA CTAAGCTTCA GCGCTCCTGC CTGGACGCAT
 651  CCCGGCTATG CAGCCCCAGT CCAGGGCAGC AAGGCAGGCC CCGTCTGCCT
 701  CTTCACCCGG AGCCTCTGCC CGCCCCACTC ATGCTCAGGG AGAGGGTCTT
 751  CTGGCTTTTT CCCAGGCTCT GGGCAGGCAC AGGCTAGGTG CCCCTAACCC
 801  AGGCCCTGCA CACAAGGGG CAGGTGCTGG GCTCAGACCT GCCAAGAGCC
 851  ATATCCGGGA GGACCCTGCC CCTGACCTAA GCCCACCCCA AAGGCCAAAC
 901  TCTCCACTCC CTCAGCTCGG ACACCTTCTC TCCTCCCAGA TTCCAGTAAC
 951  TCCCAATCTT CTCTCTGCAG AGCCCAAATC TTGTGACAAA ACTCACACAT
1001  GCCCACCGTG CCCAGGTAAG CCAGCCCAGG CCTCGCCCTC CAGCTCAAGG
1051  CGGGACAGGT GCCCTAGAGT AGCCTGCATC CAGGGACAGG CCCCAGCCGG
1101  GTGCTGACAC GTCCACCTCC ATCTCTTCCT CAGCACCTGA ACTCCTGGGG
1151  GGACCGTCAG TCTTCCTCTT CCCCCCAAAA CCCAAGGACA CCCTCATGAT
```

Fig. 11A

```
1201  CTCCCGGACC CCTGAGGTCA CATGCGTGGT GGTGGACGTG AGCCACGAAG
1251  ACCCTGAGGT CAAGTTCAAC TGGTACGTGG ACGGCGTGGA GGTGCATAAT
1301  GCCAAGACAA AGCCGCGGGA GGAGCAGTAC AACAGCACGT ACCGGGTGGT
1351  CAGCGTCCTC ACCGTCCTGC ACCAGGACTG GCTGAATGGC AAGGAGTACA
1401  AGTGCAAGGT CTCCAACAAA GCCCTCCCAG CCCCCATCGA GAAAACCATC
1451  TCCAAAGCCA AGGTGGGAC CCGTGGGGTG CGAGGGCCAC ATGGACAGAG
1501  GCCGGCTCGG CCCACCCTCT GCCCTGAGAG TGACCGCTGT ACCAACCTCT
1551  GTCCTACAGG GCAGCCCCGA GAACCACAGG TGTACACCCT GCCCCCATCC
1601  CGGGATGAGC TGACCAAGAA CCAGGTCAGC CTGACCTGCC TGGTCAAAGG
1651  CTTCTATCCC AGCGACATCG CCGTGGAGTG GGAGAGCAAT GGGCAGCCGG
1701  AGAACAACTA CAAGACCACG CCTCCCGTGC TGGACTCCGA CGGCTCCTTC
1751  TTCCTCTACA GCAAGCTCAC CGTGGACAAG AGCAGGTGGC AGCAGGGGAA
1801  CGTCTTCTCA TGCTCCGTGA TGCATGAGGC TCTGCACAAC CACTACACGC
1851  AGAAGAGCCT CTCCCTGTCT CCGGGTAAAT GAGTGCGACG GCCG
```

Fig. 11B

```
  1  MALSWVLTVL SLLPLLEAQI PLCANLVPVP ITNATLDQIT GKWFYIASAF
 51  RNEEYNKSVQ EIQATFFYFT PNKTEDTIFL REYQTRQDQC IYNTTYLNVQ
101  RENGTISRYV GGQEHFAHLL ILRDTKTYML AFDVNDEKNW GLSVYADKPE
151  TTKEQLGEFY EALDCLRIPK SDVVYTDWKK DKCEPLEKQH EKERKQEEGE
201  SDPEGEPKSC DKTHTCPPCP APELLGGPSV FLFPPKPKDT LMISRTPEVT
251  CVVVDVSHED PEVKFNWYVD GVEVHNAKTK PREEQYNSTY RVVSVLTVLH
301  QDWLNGKEYK CKVSNKALPA PIEKTISKAK GQPREPQVYT LPPSRDELTK
351  NQVSLTCLVK GFYPSDIAVE WESNGQPENN YKTTPPVLDS DGSFFLYSKL
401  TVDKSRWQQG NVFSCSVMHE ALHNHYTQKS LSLSPGK*
```

Fig. 11C

NUCLEIC ACIDS ENCODING ARTIFICIAL P-SELECTIN LIGANDS

STATEMENT AS TO FEDERALLY SPONSORED RESEARCH

This invention was made with Government support under NIH grant DK43031, and the Government therefore has certain rights in this invention.

CROSS REFERENCE TO RELATED APPLICATION

This application claims benefit from provisional application 60/000,213, filed Jun. 14, 1995 (now abandoned) U.S. Ser. No. 08/661,960, filed Jun. 12, 1996 (now abandoned).

BACKGROUND OF THE INVENTION

This invention relates to P-selectin ligand molecules, DNAs, and uses thereof.

P-selectin is an integral membrane C-type lectin found within the Weibel-Palade bodies of endothelial cells and the alpha granules of platelets (McEver et al., J. Clin. Invest., 84:92-99, 1989; Bonfanti et al., Blood, 73:1109-1112, 1989; Hsu-Lin et al., J. Biol. Chem., 259:9121-9126, 1984; Stenberg et al., J. Cell Biol., 101:880-886, 1985). Its translocation to the plasma membrane can be induced by thrombin, histamine and other mediators released by mast cell activation, complement C5b-9 complex or C5a fragment, peroxides, and oxidized low-density lipoprotein (Hsu-Lin et al., J. Biol. Chem., 259:9121-9126, 1984; Stenberg et al., J. Cell Biol., 101:880-886, 1985; Hattori et al., J. Biol. Chem., 264:9053-9060, 1989; Kubes and Kanwar, J. Immunol., 152:3570-2577, 1994; Thorlacius et al., Biochem. Biophys. Res. Communications, 203:1043-1049, 1994; Foreman et al., J. Clin. Invest., 94:1147-1155, 1994; Patel et al., J. Cell Biol., 112: 749-759, 1991; Lehr et al., Laboratory Invest., 71:380-386, 1994; Gebuhrer et al., Biochem. J., 306:293-298, 1995). Once displayed on the cell surface, P-selectin supports the attachment of myelomonocytes to platelets or endothelial cells (Larsen et al., Cell, 59:305-312, 1989; Hamburger and McEver, Blood, 75:550-554 1990; Geng et al., Nature, 343: 757-760, 1990; Gamble et al., Science, 249:414-417, 1990). In the latter setting, its appearance heralds an underlying tissue insult and supports the initial step in leukocyte extravasation, the rolling of neutrophils along the postcapillary venule wall (Lawrence and Springer, Cell, 65:859-873, 1991). Mice which are homozygously deficient for the P-selectin structural gene exhibit decreased leukocyte rolling and show delayed recruitment of granulocytes to sites of experimentally induced inflammation (Mayadas et al., Cell, 74:541-554, 1993). Generally, the mediators which induce P-selectin expression are involved in signaling trauma or wounding. One of the first recognized responses to tissue trauma is mast cell activation, which is accompanied by release of histamine, serotonin, and other diffusible mediators. Other common events include thrombus formation at sites of vascular rupture and complement alternative pathway engagement by foreign bodies. P-selectin expression is induced by signals generated in each of these contexts. Although induction of P-selectin mediated neutrophil rolling has been thought to be an inevitable consequence of surgical intervention, cromolyn, an agent which blocks mast cell degranulation, has been shown to prevent such rolling, thereby providing an elegant demonstration of the role of the mast cell as the link between trauma and extravasation (Kubes and Kanwar, J. Immunol., 152: 3570-3577, 1994).

SUMMARY OF THE INVENTION

In a first aspect, the invention features an organic molecule to which there is covalently bonded a sialyl-Le$^x$ determinant and a sulfated determinant, at least one of these determinants being positioned at a non-naturally occurring site on the molecule.

In a second aspect, the invention features a P-selectin ligand characterized by a sulfated determinant which is attached to the molecule at a sequence consisting essentially of: (a) amino acids 21-57 of FIG. 8A, (b) amino acids 38-57 of FIG. 8A, or (c) TGDYYEDSYEDIS (SEQ ID NO: 15). Such P-selectin ligands may also preferably include at least one copy of a repeat sequence ATEAQTTPPA (SEQ ID NO: 1) or MATNSLETSTGTSGPPVT (SEQ ID NO: 2).

In a third aspect, the invention features fusion proteins that include a P-selectin ligand joined to an antibody domain (for example, one or more of the hinge, CH2, and CH3 domains).

In related aspects, the invention features purified nucleic acid encoding a protein containing sites for the attachment of a sialyl-Le$^x$ determinant and a sulfated determinant, at least one of these determinants being positioned at a non-naturally occurring site on the protein; purified nucleic acid encoding any one of the P-selectin ligands of the invention; purified nucleic acid encoding a P-selectin-antibody fusion protein; and vectors and recombinant cells including any of these nucleic acids.

In another related aspect, the invention features a method of inhibiting the binding of a cell bearing a P-selectin protein to a molecule or cell bearing a sialyl-Le$^x$ determinant and a sulfated determinant. The method involves contacting the P-selectin protein-bearing cell with either an organic molecule bearing sialyl-Le$^x$ and sulfated determinants, at least one of these determinants being positioned at a non-naturally occurring site on the molecule; a P-selectin-antibody fusion protein; or any of the P-selectin ligands of the invention.

In another related aspect, the invention features a method of reducing inflammation in a mammal involving administering to the patient a therapeutically-effective amount of either an organic molecule bearing sialyl-Le$^x$ and sulfated determinants, at least one of these determinants being positioned at a non-naturally occurring site on the molecule; a P-selectin-antibody fusion protein; or any one of the P-selectin ligands of the invention.

In yet another related aspect, the invention features a method of reducing or protecting a mammal against any extravasation-dependent adverse reaction (including, without limitation, extravasation-dependent organ damage and/or clotting associated with adult respiratory distress syndrome, glomerular nephritis, and ischemic myocardial injury). The method involves administering to the mammal a therapeutically-effective amount of either an organic molecule to which there is covalently bonded a sialyl-Le$^x$ and a sulfated determinant, at least one of these determinants being positioned at a non-naturally occurring site on the molecule; a P-selectin-antibody fusion protein; or any of the P-selectin ligands of the invention.

In a final aspect, the invention features a method of reducing or protecting a mammal against an adverse immune reaction, involving administering to the mammal a therapeutically-effective amount of either an organic molecule to which there is covalently bonded a sialyl-Le$^x$ and a sulfated determinant, at least one of these determinants being positioned at a non-naturally occurring site on the molecule; a P-selectin-antibody fusion protein; or any of the P-selectin ligands of the invention. Preferably, this method involves treating the mammal for an adverse immune reaction which is induced by a microbial factor. Such microbial factors include, without limitation, gram-negative bacteria lipopolysaccharides (LPS), peptidoglycans from gram-positive organisms, mannan from fungal cell walls, polysaccharides, extracellular enzymes (e.g., streptokinase) and toxins (e.g., toxic shock enterotoxins of staphylococci). In other preferred embodiments, the method involves treating a mammal for any adverse immune reaction which is induced by a host factor. Such host factors include, without limitation, metabolites of complement, kinin, and coagulation systems, factors released from stimulated cells (e.g., cytokines such as interleukin 1 (IL-1) and tumor necrosis factor-$\alpha$ (TNF)), enzymes and oxidants from polymorphonuclear leukocytes (PMNs), vasopeptides (e.g., histamine), and products of the metabolism of arachidonic acid. In other preferred embodiments, the adverse immune reaction is induced by recombinant TNF-$\alpha$ or is induced by recombinant IL-1. In yet other preferred embodiments, the adverse immune reaction is septic shock or is septicemia.

In preferred embodiments of each of the above aspects, the organic molecule or protein also inhibits the binding of a cell bearing an E-selectin (ELAM-1) protein to a molecule or cell bearing a sialyl-Le$^x$ determinant and thus inhibits E-selectin-mediated inflammation, extravasation-dependent adverse reactions, and adverse immune reactions; the sialyl-Le$^x$ and sulfated determinants are present on a P-selectin ligand consisting essentially of: amino acids 21-57 of FIG. 8A (for example, amino acids 38-57 of FIG. 8A); the sialyl-Le$^x$ determinant is N-linked or O-linked; the molecule or protein contains multiple sialyl-Le$^x$ and/or multiple sulfated determinants; the organic molecule is a protein (for example, an antibody (for example, IgG or IgM), $\alpha_1$-acid glycoprotein (AGP), or an antibody fusion protein (for example, an AGP-antibody fusion protein); the protein is an antibody, AGP, or an antibody fusion protein (for example, an AGP-antibody fusion protein) to which any of the P-selectin ligands described herein is appended (for example, at the protein's amino-terminus); the antibody or antibody fusion protein (for example, the AGP-antibody fusion protein) includes, as an antibody portion, an IgG1 CH2, CH3, and/or hinge domain; the antibody, AGP, or antibody fusion protein includes one or more of the N-linked glycan addition sites of $\alpha_1$-acid glycoprotein; the antibody portion of the molecule bears one or more non-naturally occurring sialyl-Le$^x$ determinants; the sialyl-Le$^x$ determinant interferes with the antibody's ability to fix complement or bind an F$_c$ receptor (for example, due to a sialyl-Le$^x$ determinant attached to one or more of amino acids 274, 287, or 322 of the sequence shown in FIG. 10); and the organic molecule is soluble.

By a "P-selectin ligand", as used herein, is meant any amino acid sequence capable of mediating an interaction with the P-selectin receptor and includes those proteins referred to as P-selectin counter-receptors. Preferable P-selectin ligands contain, without limitation, tyrosine sulfation sites consisting essentially of amino acids 21-57 of FIG. 8A, amino acids 38-57 of FIG. 8A, or the sequence TGDYYEDSYEDIS (SEQ ID NO: 15). P-selectin ligands according to the invention may be used in conjunction with additional protein domains (for example, antibody domains) to produce fusion proteins useful in the invention.

By "non-naturally occurring" is meant a sialyl-Le$^x$ or sulfated determinant that is not one which is naturally bound to the molecule at that amino acid location.

By "inflammation" is meant a pathologic process consisting of cytologic and histologic reactions that occur in the affected blood vessels and adjacent tissues in response to an injury or abnormal stimulation caused by a physical, chemical, or biologic agent. Inflammation, as used herein, includes any acute inflammatory response (for example, during or following adult respiratory distress syndrome or ischemic myocardial injury) as well as any chronic inflammatory response (for example, rheumatoid arthritis, psoriasis, or pemphigus vulgaris).

By "purified nucleic acid" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "N-linked" is meant bonded to the amide nitrogen of an asparagine residue of a protein.

By "O-linked" is meant bonded to the hydroxyl-group oxygen of a serine, threonine, or hydroxylysine residue of a protein.

By an "extravasation-dependent adverse reaction" is meant any reaction which is detrimental to the host and which results directly or indirectly from the inappropriate attachment of neutrophils to endothelium at or proximate to a site of inflammation, tissue damage, or thrombus formation and results in migration of those neutrophils into the attached blood vessel or organ. Organs which may be affected by such damage include, without limitation, the heart, lungs, and kidneys.

By an "adverse immune reaction" is meant any reaction mediated by an immune cell (i.e., any B cell, T cell, monocyte/macrophage, natural killer cell, mast cell, basophil, or granulocyte) and which is detrimental to the host.

BRIEF DESCRIPTION OF THE DRAWINGS

The drawings will first be briefly described.

NH$_2$/CD43 "repeats" are represented by SEQ ID NO:2. PSGL-1 was fused to the N-terminus of the predicted mature CD34 and GlyCAM-1 molecules, and to the N-terminus of the repeat region of CD43.

FIG. 6A is a histogram representing binding of cells to P-selectin. FIG. 6B is a histogram representing binding of cells to E-selectin.

FIG. 10 is a listing of the nucleotide sequence (SEQ ID NO:8) encoding IgG1 (SEQ ID NO:9) and mutations designed to create N-linked glycan addition sites (SEQ ID NO:12).

FIG. 11A is the nucleotide sequence (SEQ ID NO: 10) of an AGP-IgG1 fusion protein.

FIG. 11B is the amino acid sequence (SEQ ID NO: 11) of an AGP-IgG1 fusion protein.

In FIG. 15, construct "1R1-WT" is equivalent to "1R1" of FIG. 4A, and construct "CD43-WT" is equivalent to "PSGL-1-NH$_2$/CD43-COOH" of FIG. 2A.

DETAILED DESCRIPTION OF THE INVENTION

Figure 1A:
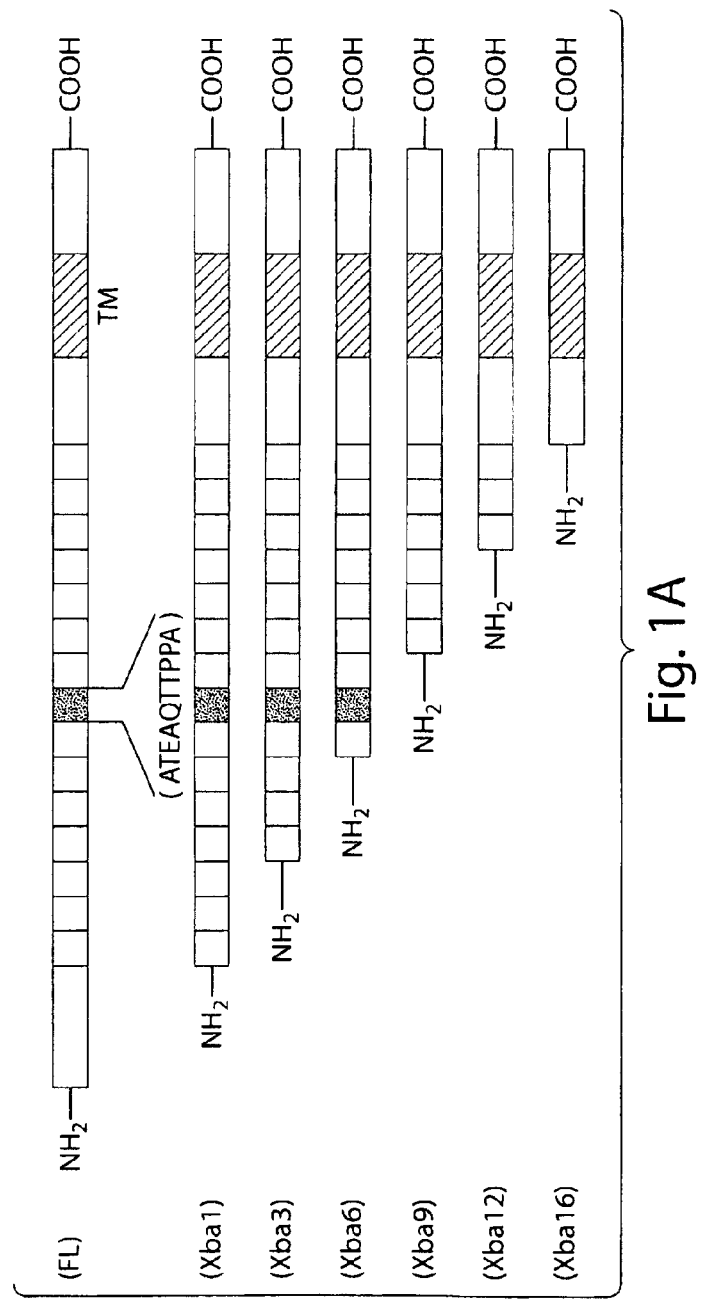
FIG. 1A is a schematic representation of the structure of the PSGL-1 deletion mutants. Systematic deletion of the ectodomain of PSGL-1 was accomplished with conventional PCR methods. A representative 10-residue repeat (stippled; SEQ ID NO:1) and the transmembrane domain (hatched) are illustrated.

Sialyl-Lewis X (sialyl-Le$^x$) and sulfated determinants were shown to interact with P-selectin and facilitate binding by the following experiments. These examples are presented to illustrate, not limit, the invention. The methods used in the following experiments will first be described.

Production of Soluble P-Selectin

P-selectin and E-selectin Ig chimeras were prepared by transient expression in COS cells of an expression plasmid encoding the lectin, EGF-related, and first two short consensus repeat related domains of P-selectin joined to the hinge, CH2, and CH3 domains of human IgG1 (Aruffo et al., EMBO J., 6:3313-3316, 1991; Walz et al., Science, 250:1132-1135, 1990). The PSGL-1 cDNA coding sequence was obtained by PCR amplification of an HL-60 cDNA library, and the sequence confirmed by DNA sequencing. The coding segment for the mature extracellular, transmembrane, and intracellular domains was inserted into an expression vector based on CDM8 which lacks the polyoma virus origin of replication and contains the leader sequence for the CD5 antigen positioned just upstream of the coding region for an influenza hemagglutinin (flu) peptide (Field et al., Mol. Cell. Biol. 8:2159-2165, 1988) epitope tag.

Construction of PSGL-1 Deletions

Amino terminal PSGL-1 deletion constructs were prepared by PCR amplification using primers encoding the desired endpoint of the deletion mutant located downstream of an XbaI site in frame two (encodes Leu Asp). The resulting sequences encoded a polypeptide in which the residues listed below immediately followed the aspartic acid (D) of the Xba site: A118, A128, A138, A148, A158, A168, G178, A188, A198, A208, A218, A228, A238, A248, A258, and T268 of the PSGL-1 precursor. The PCR fragments were then inserted in the CD5 leader flu tag expression vector used for expression of the intact PSGL-1. The flu tag terminates in an XbaI site in the frame described above. Sequences at the flu tag junction were verified, and expression was confirmed in COS cells by indirect immunofluorescence microscopy and flow cytometry. A series of internal deletions with an EcoRI site at the site of the deletion in frame one (encodes glutamic acid phenylalanine) was also prepared by first creating deletion variants with amino termini (residues immediately following phenylalanine (F)) of the EcoRI site corresponding to A118, A128, A138, A148, A158, A168, G178, A188, A198, A208, A218, A228, A238, A248, and A258 of the peptide sequence of the precursor. To each of these deleted variants was appended a flu-tagged amino-terminal PSGL-1 domain ending with an EcoRI site in the glutamic acid phenylalanine frame immediately downstream of PSGL-1 precursor A117. The resulting constructs contained deletions between A117 and the various endpoints above.

Mucin Domain Interchanges

CD34, CD43, and GlyCAM-1 mucins were prepared for addition of the PSGL-1 amino-terminal domain by appending an EcoRI site to either the mature amino terminus (CD34 or GlyCAM-1), or to the beginning of a region of threonine/proline-rich repeats (CD43). As above, the EcoRI site was in the frame glutamic acid phenylalanine (frame 1). The CD34 sequence began at residue F30 of the precursor, the GlyCAM-1 at precursor L19, and the CD43 at precursor I135. To each of these was appended the flu-tagged PSGL-1 domain terminating in EcoRI as above. The amino terminus and repeat elements of PSGL-1 were appended to the membrane proximal, transmembrane, and intracellular domains of CD43 through an EcoRI site in the glutamic acid phenylalanine frame positioned immediately upstream of the sequences S225 of the (SEQ ID NO:17). The complementary fragment from PSGL-1 corresponded to the amino-terminal residues of the precursor up to T267.

Fine Structure Mapping of the Amino-Terminal Domain

A similar strategy was employed for the construction of deletions in the amino-terminal domain, in which PCR generated deletions were formed using primers bearing an XbaI site in the leucine aspartic acid frame (frame 2). Immediately downstream of the residues encoding aspartic acid were the PSGL-1 sequences corresponding to precursor R38, E58, P78, and A98. For the definition of the amino-terminal domain, duplex oligonucleotides were synthesized corresponding to the residues between 38 and 57 with the indicated sequence changes to mutate threonine or tyrosine residues to alanine or phenylalanine. All constructs were confirmed by dideoxy sequencing.

Cell Adhesion Assays

Transfected cells were detached from culture dishes with 0.5 mM EDTA in phosphate buffered saline (PBS) 48 to 60 hours after transfection. The cells were then loaded with 100 µl $^{51}CrO_4$ (1 mCi/ml; DuPont, Boston, Mass.) in 0.9% NaCl plus 100 ml medium by incubating them at 37° C. for 1 hour. Loaded cells were washed twice in PBS and resuspended in 0.2% BSA, 0.15 M NaCl, 3 mM $CaCl_2$. Variation in labeling rate (counts incorporated per cell) between cells prepared in parallel with the same batch of labeled chromate was typically minimal. The labeled cells were incubated in wells of 96-well microculture plates which had been coated with affinity purified goat anti-human IgG antibody (100 µl of 20 µg/ml anti-human IgG Fc (heavy chain specific) in PBS) for 2 hours in a humid chamber at room temperature. After the plate was washed twice with PBS, additional protein-binding sites were blocked by an overnight incubation with 200 µl 3% BSA in PBS. The plate was washed with PBS four times and incubated with 200 µl of fusion protein supernatants for 2 hours. Following three PBS washes and one additional wash (in 0.2% BSA, 0.15 M NaCl, 3 mM $CaCl_2$), $2\times10^5$ cells/well (in 200 µl 0.2% BSA, 0.15 M NaCl, 3 mM $CaCl_2$) were added and allowed to bind for 15 minutes at room temperature while the plate rotated on a rotary platform (80 rpm). The plate was washed three times by filling the wells with 200 µl 0.15 M NaCl/3 mM $CaCl_2$ and then inverting the plate. Adherent cells were lysed by the addition of 200 µl 2% SDS, and labeled chromate was counted with a gamma ray spectrometer.

Immunofluorescence Analysis

Cells were prepared for cytometry by incubation with the primary monoclonal antibody (a 1:200 dilution of ascites or 5 µg/ml of purified antibody is suitable) in PBS containing 3% BSA for 30 to 45 minutes. The cells were washed twice with PBS and incubated with 2 µg/ml FITC-conjugated affinity purified antibody to either mouse IgG (12CA5) or mouse IgM (CSLEX-1) for 30 to 45 minutes in PBS/3% BSA. The cells were then washed twice with PBS and resuspended in 1 ml of 1% freshly depolymerized paraformaldehyde in PBS prior to analysis. For immunofluorescence microscopy, transfected cells were fixed with 4% freshly depolymerized paraformaldehyde, washed, exposed to BSA at 3% in PBS for 30 minutes, and then incubated with primary antibody (ascites, 1:250) for 30-45 minutes. The cells were then washed twice with PBS and incubated for 30-45 minutes with FITC-conjugated affinity-purified antibody to mouse IgG (Cappell; 2 µg/ml in PBS containing 3% BSA). Finally, the cells were washed twice with PBS and analyzed.

Metabolic Labeling with $^{35}SO_4$

COS cells transfected with expression plasmids encoding mucin:immunoglobulin chimeras were trypsinized one day after transfection and transferred to new plates in complete medium (DMEM with 10% calf serum). Prior to labeling, the medium was removed, the cells were washed once with PBS, and the medium was replaced with either cysteine and methionine-free medium for labeling with [$^{35}S$]cysteine and methionine (TransLabel, ICN) or with sulfate-free CRCM-30 medium (Sigma Chemical Co.) for labeling with $^{35}SO_4$. Serum was not added, and radionuclide was typically present at a concentration of 200 µCi/ml. After a labeling interval of 12 to 16 hours, the supernatants were harvested, and the fusion proteins were collected by adsorption to goat anti-human IgG agarose (Cappel). Adsorbed proteins were subjected to denaturing electrophoresis on 8% polyacrylamide gels under reducing conditions.

Chlorate Inhibition of Adhesion

COS cells were transfected with DEAE dextran and incubated immediately in DMEM containing 10% calf serum and 10 mM sodium chlorate. One day after transfection the cells were trypsinized and incubated in fresh dishes in the same medium for 6 hours. The medium was then removed, the cells were washed with PBS, and then incubated for 18 additional hours in a custom prepared DMEM medium (Life Technologies) lacking sulfate and containing 2% of the conventional levels of cysteine and methionine with 10% dialyzed fetal bovine serum in the presence of 10 mM sodium chlorate (Baeuerle and Huttner, Biochem. Biophys. Res. Comm., 141: 870-877, 1986). Cells were then harvested for use in the adhesion and immunofluorescence assays. Control cells were treated similarly but were incubated in DMEM containing undialyzed serum.

HL-60 Cell Rolling

Video images of HL-60 cells rolling through a parallel plate rectangular flow chamber (FCS2, Bioptechs, Incorporated, Butler, Pa.) with a temperature controlled stage set at 37° C. were acquired with an AIMS Technology (Bronx, N.Y.) CCD™ camera mounted on a Zeiss ICM 405 inverted microscope equipped with a 2.5× objective. The chamber height was 250 μm. Cells were withdrawn through the chamber at a defined flow rate with the aid of a Harvard Apparatus (South Natick, Mass.) model I/W 22 syringe pump. Images were analyzed using NIH Image. To inhibit sulfation, HL-60 cells were washed once with PBS and grown for 18 hours in sulfate-free medium containing 2% of the normal levels of cysteine and methionine, 10 mM sodium chlorate, and dialyzed serum as described above. For each experiment, $10^{16}$ cells were suspended in 1 ml of 0.15 M NaCl, 3 mM $CaCl_2$ and drawn through the chamber. Glass coverslips were coated with affinity-purified goat anti-human IgG antibody at a concentration of 10 μg/ml in 50 mM Tris-HCl (pH 9.0) for 2 hours, washed twice with PBS, and blocked overnight with 0.2% BSA in PBS. The treated coverslips were then immersed in supernatants of COS cells transfected with the appropriate immunoglobulin chimera expression plasmids, washed twice with PBS, and assembled in the flow chamber.

Construction of a Preferred Synthetic P-Selectin Ligand

To create a synthetic molecule which has the capacity to act as a P-selectin ligand, a synthetic oligonucleotide was created which encoded the sequence residues of human coagulation Factor VIII constituting the tyrosine sulfation site of that molecule. The Factor VIII residues were TGDYYEDSYEDIS (SEQ ID NO: 15), and the sequence corresponded to that of native Factor VIII except for the inclusion of an EcoRV site at the 3' end, encoding the Asp and Ile residues, which was included in the oligo for convenience of monitoring the cloning step. The Factor VIII tyrosine sulfation sequence was inserted between the flu hemagglutinin oligopeptide tag (described above) and the amino-terminus of the human CD43 mucin derivative (also described above).

In addition, other test constructs were generated. In particular, the above-described Factor VIII tyrosine sulfation sequence was also inserted between the flu hemagglutinin tag and the amino-terminus of the 1R1 construct described above. And an oligonucleotide encoding the tyrosine sulfation site of the fourth component of human complement (EDYEYDELP; SEQ ID NO: 16) was inserted in the CD43 and 1R1 constructs at a position comparable to the Factor VIII oligonucleotide (described above). Each of these constructs is depicted diagrammatically in FIG. 14.

The Amino Terminus of PSGL-1 is Necessary for P-Selectin Binding

Figure 1B:
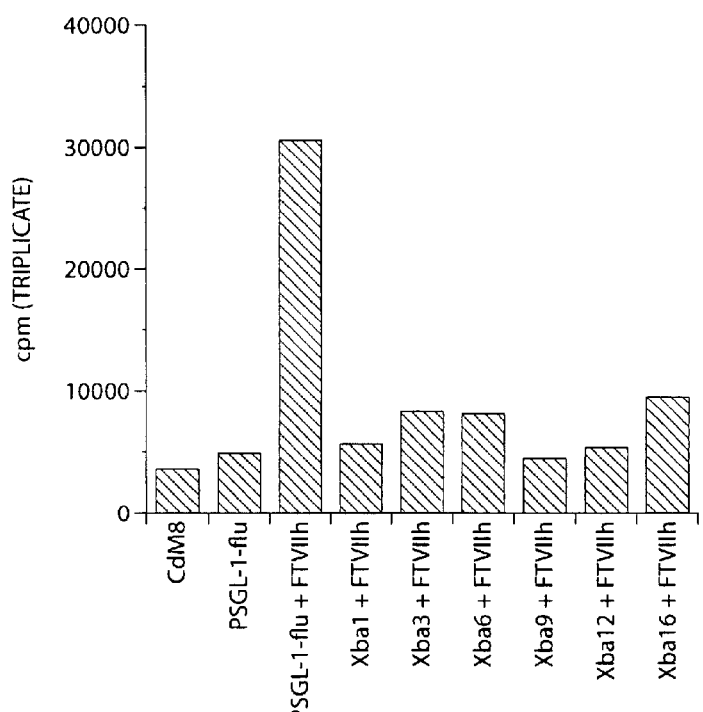
FIG. 1B is a histogram which represents P-selectin binding activity of transfected COS cells expressing the deletions shown in FIG. 1A. $^{51}$Cr-labeled cells were allowed to adhere to soluble P-selectin adsorbed to microtiter wells. The cells were washed, the bound cells were then lysed, and $^{51}$Cr levels were counted. Deletion constructs were introduced into cells either in the absence (bar 2) or presence (remaining 7 bars) of the human FTVII fucosyltransferase.

Deletions of the amino terminus of the PSGL-1 mucin were created with PCR techniques, and the resulting truncated cDNAs were inserted downstream of a secretory peptide sequence which had been fused to a short oligopeptide tag derived from influenza hemagglutinin (HA). Expression plasmids encoding the truncated molecules (FIG. 1A) were transfected into COS cells in the presence of a specific myeloid fucosyltransferase, designated FTVII, which directs the expression of $sLe^x$ determinants exclusively (Sasaki et al., J. Biol. Chem., 269:14730-14737, 1994; Natsuka et al., [published erratum appears in J. Biol. Chem, 269:20806, 1994], J. Biol. Chem., 269:16789-16794, 1994). Expression of the deletion mutants at the cell surface was confirmed by indirect immunofluorescence using anti-HA monoclonal antibodies. The presence of $sLe^x$ on the cell surface was similarly confirmed using the monoclonal antibody CSLEX-1. The ability of radiolabeled transfected cells to bind to plastic wells precoated with P-selectin:immunoglobulin fusion protein was determined. These experiments revealed that deletion of the amino terminal 100 residues (referred to herein as the apical domain) of PSGL-1 was sufficient to abolish binding of the transfectants to immobilized P-selectin (FIG. 1B). These experiments also demonstrate that $sLe^x$ mediates P-selectin binding, as expression of FTVII was required for P-selectin binding (FIG. 1B; compare bar 2 with bar 3). Expression of the deletion variants at the cell surface was confirmed by indirect immunofluorescence using anti-HA monoclonal antibodies, and the presence of $sLe^x$ on the cell surface was confirmed using the monoclonal antibody CSLEX-1. Table 1 shows the mean fluorescence intensity (MFI) of COS cells that were cotransfected with human FTVIIh and the deletion constructs (shown in FIG. 1A), and subjected to indirect immunofluorescence with antibody against the amino terminal flu peptide or $sLe^x$.

TABLE 1

| Construct | Expression (MFI) | |
|---|---|---|
| | Flu | $Sle^x$ |
| PSGL-1-flu | 5.0 | 37 |
| Xba1 | 17.0 | 26 |
| Xba3 | 20.0 | 28 |
| Xba6 | 21.0 | 28 |
| Xba9 | 12.0 | 26 |
| Xba12 | 6.0 | 30 |
| Xba16 | 6.0 | 25 |

Figure 2A:
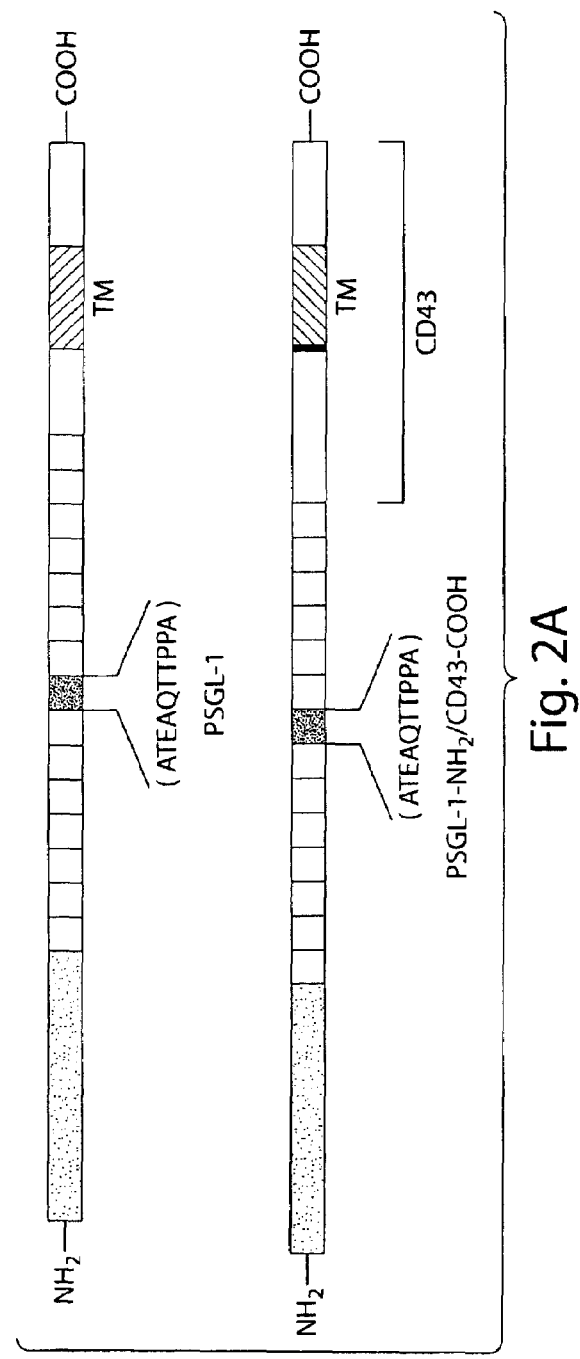
FIG. 2A is a schematic representation of chimeras of PSGL-1 and CD43 (SEQ ID NO:1). The membrane proximal extracellular domain, transmembrane, and intracellular domains of PSGL-1 were replaced with the cognate sequences of CD43 (SEQ ID NO:17). The resulting molecule lacks cysteines and thus cannot form a disulfide linked dimer.
Figure 2B:
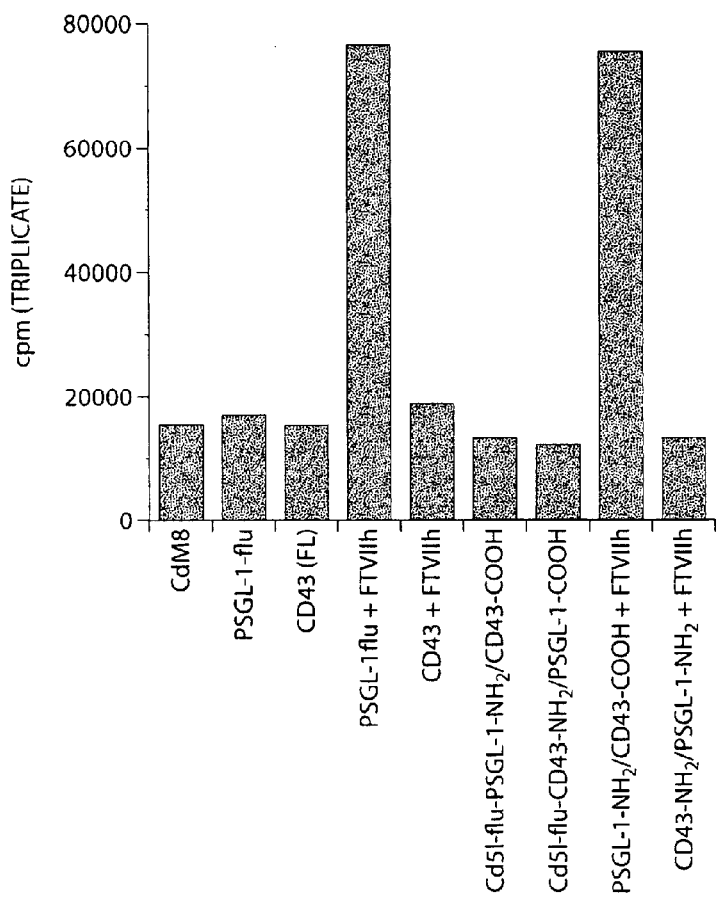
FIG. 2B is a histogram representing P-selectin binding activity of transfected COS cells expressing the chimeras shown in FIG. 2A. FTVIIh, cotransfection with the human FTVII fucosyltransferase.

In the Context of Large, Sulfated Mucins, the Amino Terminus of PSGL-1 is Sufficient for P-Selectin Binding To determine whether PSGL-1 sequences other than those found in the first 100 N-terminal amino acids (i.e., the apical domain) of PSGL-1 were required for binding to P-selectin, the transmembrane and cytoplasmic regions of PSGL-1 were replaced with those of the CD43 antigen (Pallant et al., Proc. Natl. Acad. Sci., 86:1328-1332, 1989; Shelley et al., Proc. Natl. Acad. Sci., 86:2819-2823, 1989). The resulting molecule, which did not contain cysteine residues, bound P-selectin with the same efficiency as PSGL-1 did (FIG. 2A and FIG. 2B). Thus, neither disulfide bond formation nor a specific membrane anchoring segment is required for P-selectin binding activity.

Figure 3A:
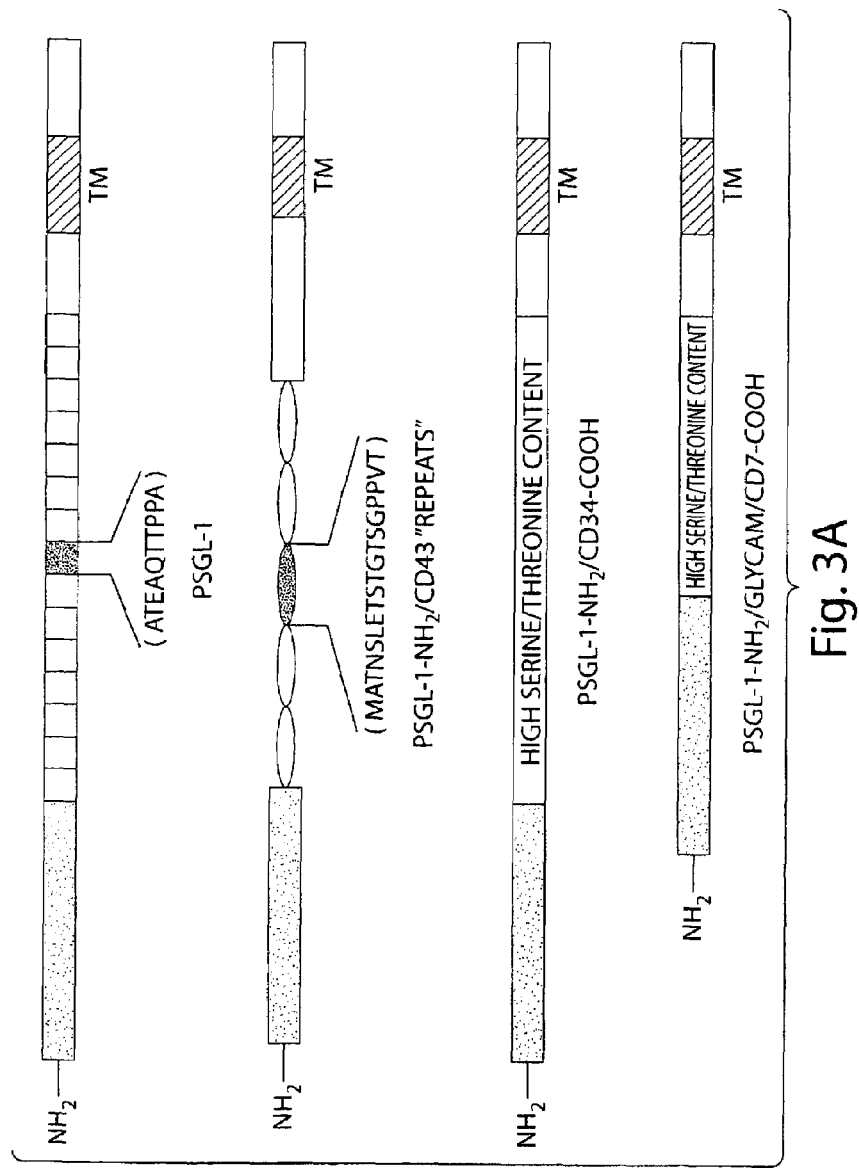
FIG. 3A is a schematic representation of chimeric mucins bearing the PSGL-1 apical domain appended to intact or truncated mucin C-termini. The PSGL-1 N-terminus (stippled; SEQ ID NO:1) and the transmembrane (TM) domains (hatched) are illustrated. The sequence of PSGL-1-
Figure 3B:
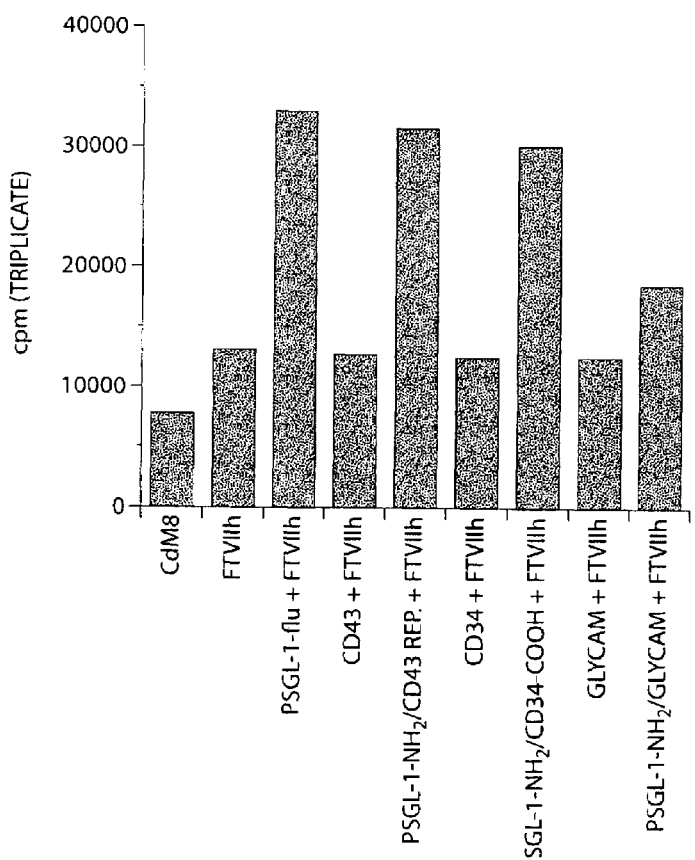
FIG. 3B is a histogram representing P-selectin binding activity of transfected COS cells expressing the constructs shown in FIG. 3A. FTVIIh, human FTVII fucosyltransferase.

The predicted first 100 amino acids of PSGL-1 were then genetically grafted onto the amino termini of mucin-like repeat elements of several unrelated mucins to determine whether or not the PSGL-1 apical domain is sufficient for P-selectin ligand (i.e., counterreceptor) activity (FIG. 3A). Certain of these chimeric mucins were able to support P-selectin binding in this setting. CD34 and CD43, two relatively large mucins found predominantly on human hematopoietic cells, were both able to support binding. In contrast, an artificially anchored variant of GlyCAM-1, a mucin expressed on high endothelial venules that has L-selectin ligand activity (Lasky et al., Science, 258:964-969, 1992), was inactive in this assay (FIG. 3B). The GlyCAM-1 mucin domain in these experiments was tethered to the cell surface via the extracellular stalk, transmembrane domain, and cytoplasmic anchoring segments of CD7 (Aruffo et al., EMBO J., 6:3313-3316, 1987). Cell surface expression of the different mucins and mucin chimeras was confirmed by indirect immunofluorescence using antibodies agains flu tag, sLe$^x$, or the respective mucins. Table 2 shows mean fluorescence intensity (MFI) measurements of expression of flu tag or sLe$^x$ by COS cells transfected with the constructs analyzed in FIG. 3B. CD34 and CD43 constructs were positive for expression by indirect immunofluorescence using cognate anti-CD antibodies.

TABLE 2

| Construct | Expression (MFI) | |
|---|---|---|
| | Flu | SLeX |
| FTVIIh | — | 52 |
| PSGL-1-flu | 9.8 | 43 |
| CD43 | — | 60 |
| PSGL-1-NH$_2$/CD43 rep. | 12 | 67 |
| CD34 | — | 50 |
| PSGL-1-NH$_2$/CD34-COOH | 8.0 | 33 |
| Glycam-flu | 12 | 32 |
| PSGL-1-NH$_2$/Glycam-COOH | 8.0 | 28 |

Figure 4A:
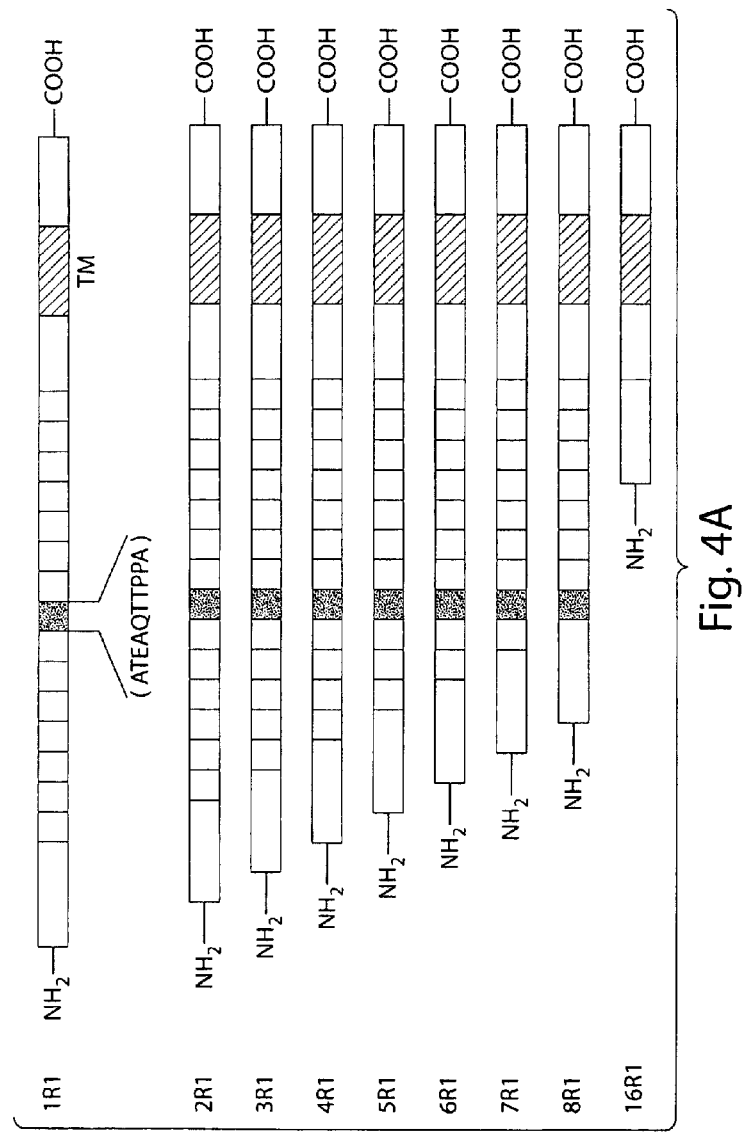
FIG. 4A is a schematic representation of PSGL deletion mutants. The amino terminal domain was appended to PSGL molecules having varying numbers of the repeated element (SEQ ID NO:1).
Figure 4B:
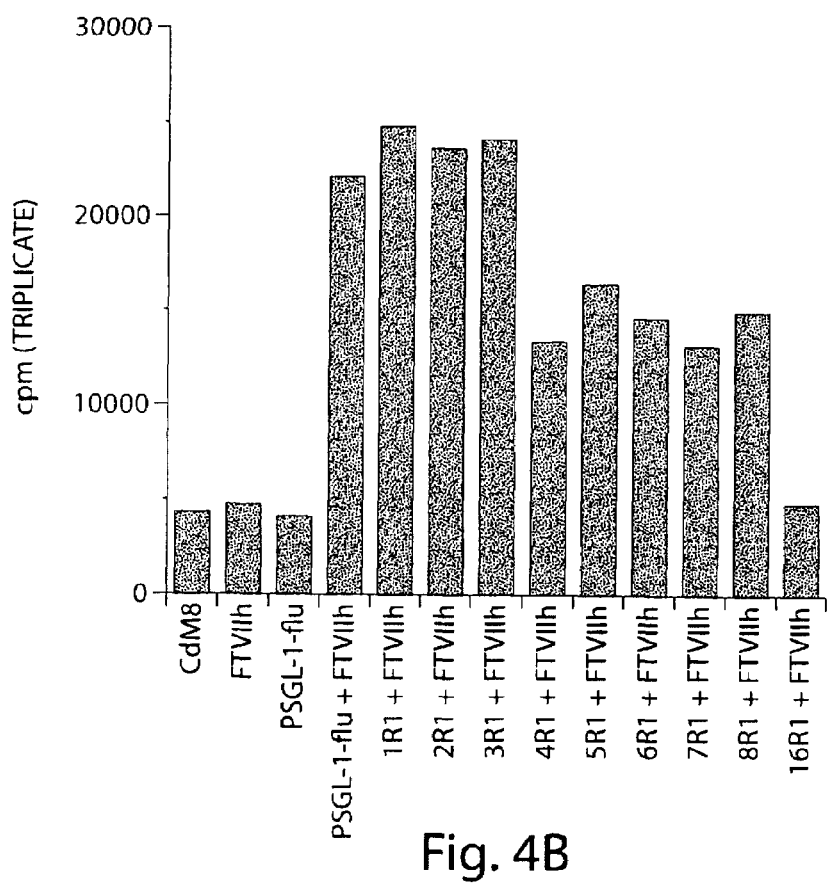
FIG. 4B is a histogram representing P-selectin binding activity of transfected COS cells expressing the chimeras illustrated in FIG. 4A.

The apparent molecular masses of CD43 and CD34 expressed in COS cells are reported to be 100-130 kD (Shelley et al., Proc. Natl. Acad. Sci., 86:2819-2823, 1989) and 100 kD (Simmons et al., J. Immunol., 148:267-271, 1992), respectively; the PSGL-1 monomer exhibits an effective molecular mass of 110 kD (Sako et al., Cell, 75:1179-1186, 1993). GlyCAM-1, in its native (untethered) state comigrates with 50 kD proteins, suggesting that it is substantially smaller (Lasky et al., Science, 258:964-969, 1992). In our studies, the larger mucins were able to support P-selectin binding when the apical domain of PSGL-1 was appended to the amino terminus of the mucins. Sequential deletion of the internal repeat elements of PSGL-1 allowed us to shorten the molecule in a systematic manner without compromising potential global tertiary associations (FIG. 4A). As these repeat elements were deleted, the binding activity of PSGL-1 declined, consistent with the conclusion that distance from the plasma membrane is an important determinant of P-selectin binding activity (FIG. 4B).

Figure 5:
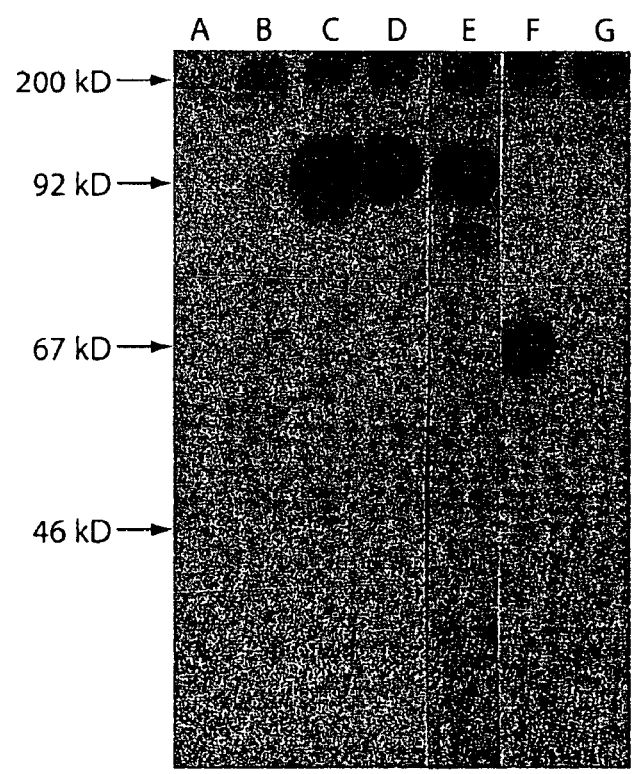
FIG. 5 is a photograph of an autoradiogram of mucin: immunoglobulin fusion proteins labeled with $^{35}$S-sulfate and electrophoresed on an 8% denaturing polyacrylamide gel under reducing conditions. Lane A, supernatant of CDM8 transfected cells; Lane B, supernatant of cells transfected with Ig expression vector (no mucin insert); Lane C, supernatant of cells expressing PSGL-1:Ig; Lane D, supernatant of cells expressing CD43:Ig; Lane E, supernatant of cells expressing CD34:Ig; and Lane F, supernatant of cells expressing GlyCAM-1:Ig.

Our data also indicate that sulfation is one determinant of the ability of mucins to support apical domain-directed binding. We assessed the ability of various mucins to undergo sulfation in COS cells. PSGL-1, CD34, CD43, and GlyCAM-1 soluble mucin chimeras readily incorporated sodium $^{35}$S-sulfate when expressed in COS cells (FIG. 5).

Inhibition of Sulfation Blocks PSGL-1 Binding to P-Selectin

Figure 6A:
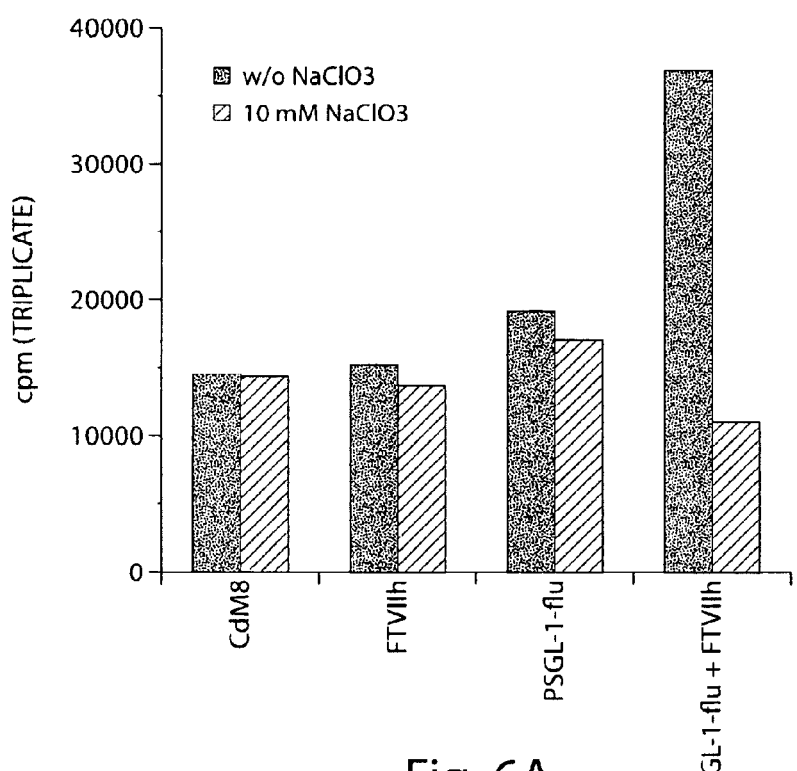
FIG. 6A and FIG. 6B are histograms representing binding to immobilized P- and E-selectin of COS cells expressing PSGL-1 with or without fucosyltransferase and in the presence or absence of 10 mM NaClO$_3$.
Figure 6B:
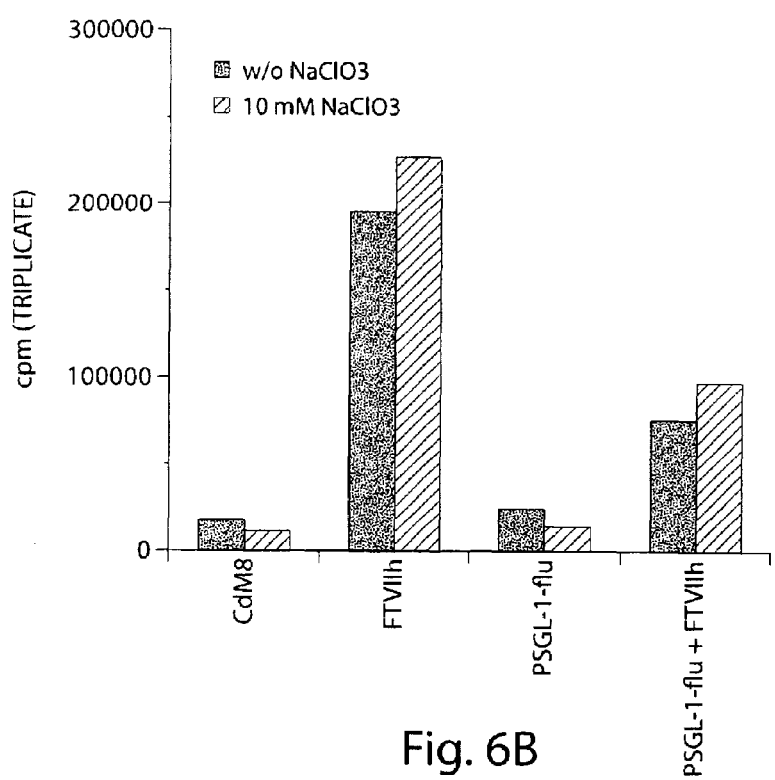

We have found that inhibition of sulfation blocks PSGL-1 binding to P-selectin. COS cells were cotransfected with PSGL-1 and FTVII, or transfected with PSGL-1 and FTVII separately. During the time period in which maximum synthesis of PSGL-1 was expected, the cells were incubated in a modified DMEM medium lacking sulfate and containing 10 mM sodium chlorate, a relatively selective inhibitor of sulfation (NaClO$_3$). We observed a significant decrease in the ability of chlorate-treated cotransfected cells to bind to immobilized P-selectin (FIG. 6A), whereas the same cells showed little or no decrement in binding to immobilized E-selectin (FIG. 6B). Cell surface expression of either the sLe$^x$ antigen and the PSGL-1 amino terminal tag sequence was not inhibited by NaClO$_3$ treatment. In fact, as shown in Table 3, an increase in the mean fluorescence intensity of the transfected cells, representing both anti-sLe$^x$ and anti-flu tag, was observed following chlorate treatment, suggesting that chlorate may affect internalization or cell surface export.

TABLE 3

| | Expression (MFI) | | | |
|---|---|---|---|---|
| | w/o NaClO$_3$ | | w/10 mM NaClO$_3$ | |
| | sLe$^x$ | Flu | sLe$^x$ | Flu |
| FTVIIh | 23 | — | 30 | — |
| PSGL-1-flu | — | 9 | — | 22 |
| PSGL-1flu + FTVIIh | 15 | 10 | 35 | 34 |

Figure 7:
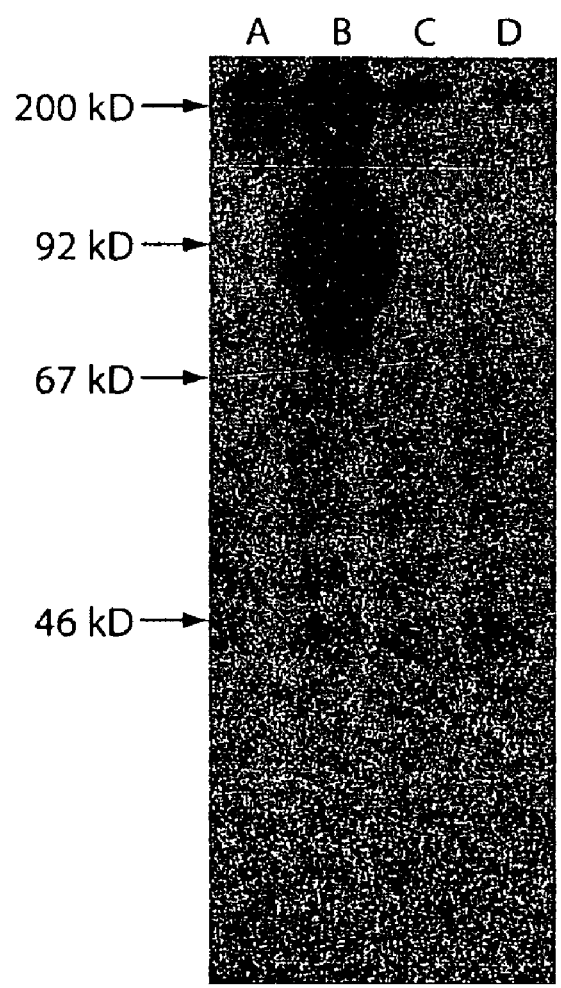
FIG. 7 is a photograph of an autoradiogram of PSGL-1: immunoglobulin fusion proteins labeled with $^{35}$S-sulfate in the presence or absence of 10 mM NaClO$_3$ and electrophoresed on an 8% denaturing polyacrylamide gel under reducing conditions. The photograph indicates that chlorate inhibits incorporation of $^{35}$S-sulfate into soluble mucin chimeras. Lane A, supernatant of CDM8 transfected cells in the absence of chlorate; Lane B, supernatant of cells expressing PSGL-1:Ig in the absence of chlorate; Lane C, supernatant of CDM8 in the presence of chlorate; and Lane D, supernatant of cells expressing PSGL-1:Ig in the presence of chlorate.

A soluble PSGL-1 immunoglobulin chimera synthesized under comparable conditions showed essentially complete inhibition of $^{35}$S-sulfate incorporation (FIG. 7), under conditions in which protein synthesis as measured by [$^{35}$S]cysteine and methionine incorporation was not inhibited. These data demonstrate that sulfation of the P-selectin ligand is required for P-selectin binding activity.

Fine Structure Deletion Analysis of the Apical Domain of PSGL-1

Figure 8A:
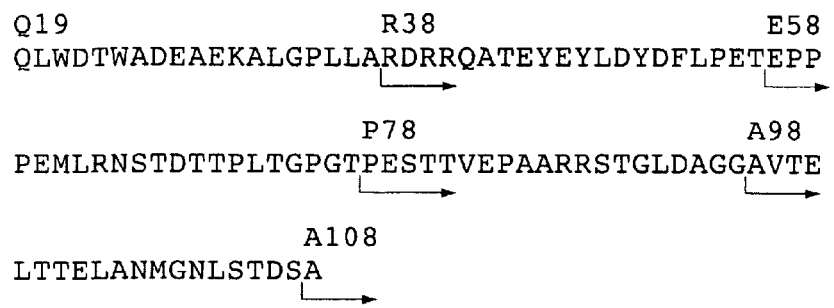
FIG. 8A is a listing of the sequence endpoints of various PSGL-1 deletion mutants (indicated by the arrows) The uppermost sequence is SEQ ID NO:3; the middle sequence is SEQ ID NO:13; the lowermost sequence is SEQ ID NO:14.
Figure 8B:
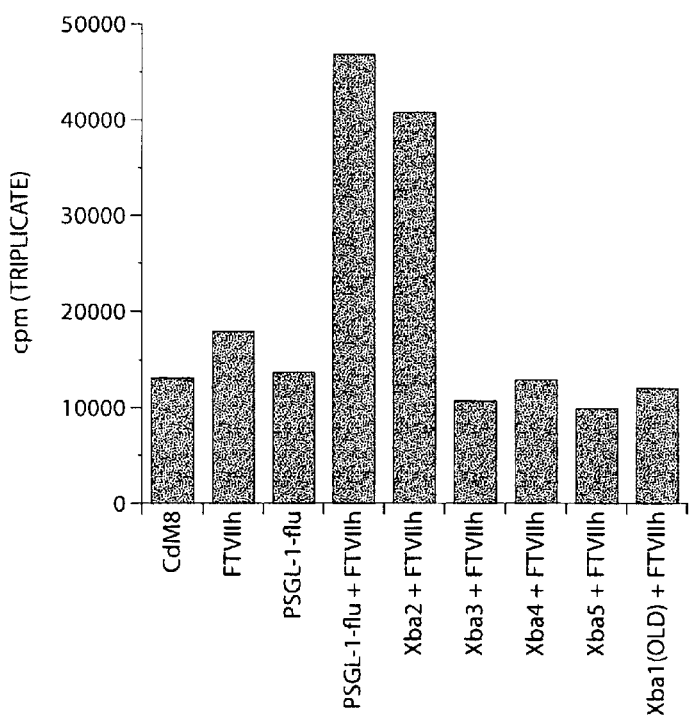
FIG. 8B is a histogram representing P-selectin binding activity of transfected COS cells expressing the deletion mutants having the endpoints shown in FIG. 8A.

To localize the elements within the 100 amino acid apical domain which contribute to P-selectin ligand activity, we prepared a collection of deletion mutants in which various regions of the apical domain were deleted (FIG. 8A). Each amino terminal deletion mutant was then placed downstream of the CD5 leader/flu tag element to monitor cell surface expression. The fine structure deletion mutants showed little variability in their ability to express the epitope tag, as assessed by indirect immunofluorescence. Removal of the first 20 amino acids of the N-terminus of the mature PSGL-1 did not affect P-selectin binding activity. In contrast, removal of the first 40 amino acids of the N-terminus abrogated binding (FIG. 8B). Further deletions of PSGL did not affect P-selectin binding activity. Accordingly, amino acid residues 20 to 40 of PSGL (i.e., residues 38 to 57 of the predicted precursor having the signal sequence) are required for P-selectin binding.

Figure 9A:
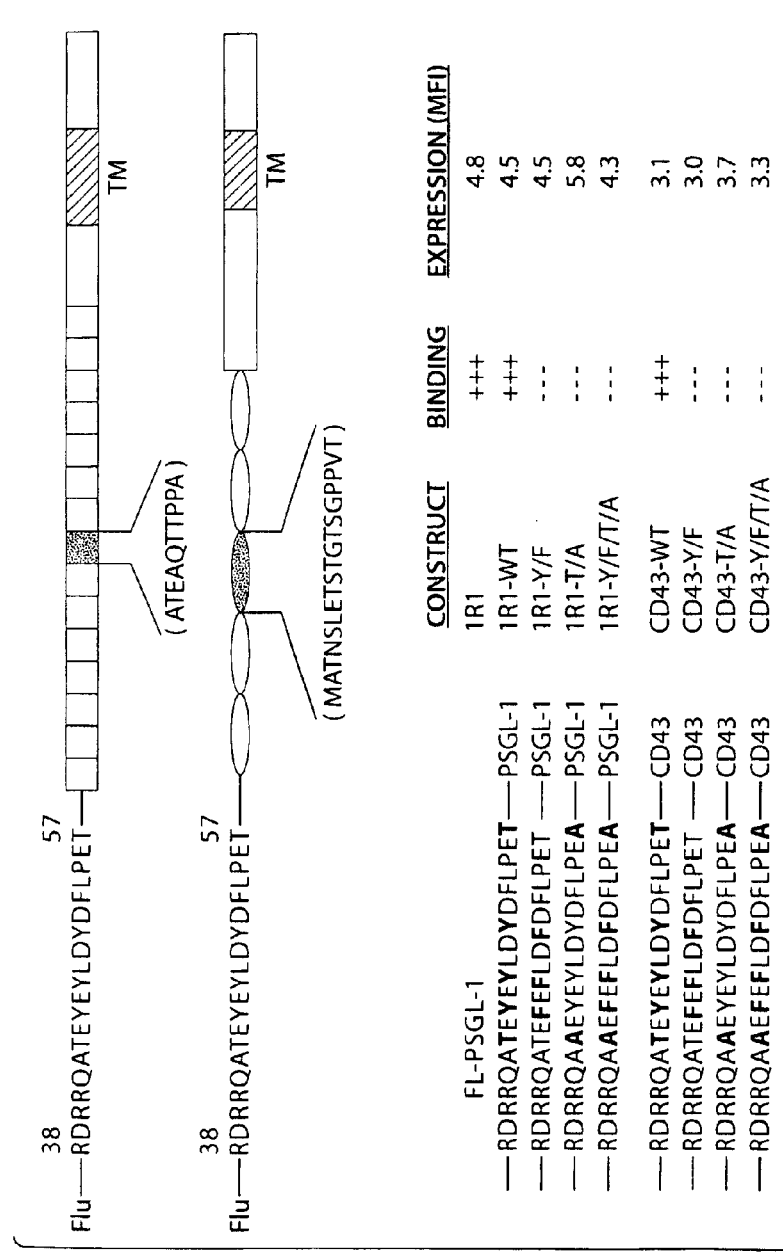
FIG. 9A is a schematic diagram of the constructs employed to measure the effect of appending wildtype and mutant variants of PSGL-1 residues 38-57 to deleted PSGL-1 or CD43 (SEQ ID NOS:1, 2 and 4-7). The inserted sequences are shown at bottom left (SEQ ID NOS:4-7).
Figure 9B:
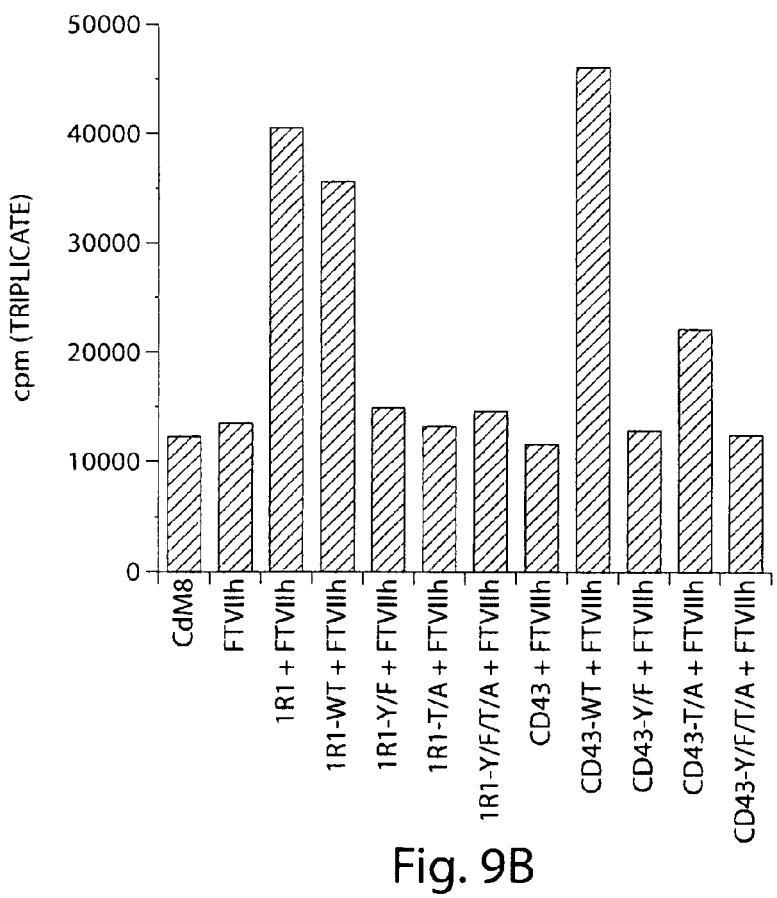
FIG. 9B is a histogram representing P-selectin binding activity of transfected COS cells expressing the chimeras illustrated in FIG. 9A.

To demonstrate that residues 38 to 57 are sufficient for PSGL-1 apical domain-directed activity, we appended this segment to the amino termini of PSGL-1 and CD43 mucin cores from which the apical domains had been deleted (FIG. 9A). In both cases, addition of amino acids 38-57 of PSGL-1 peptide element conferred P-selectin binding activity upon the mucin core. In both cases, the level of P-selectin binding activity was equivalent to that of native PSGL-1 (FIG. 9B).

Specific Residues within the Amino Terminal Peptide are Required for P-Selectin Binding Activity The 20 amino acid region which is necessary for P-selectin binding contains three potential tyrosine sulfation sites and two threonine residues for O-linked glycosylation. To assess the importance of these residues, the tyrosines were converted to phenylalanine (FIG. 9A). In a second peptide, the threonines were converted to alanines. In addition, a third peptide, containing a quintuple mutation, was prepared such that both conversions were made in a single peptide. Each mutated peptide was then positioned, separately, downstream of the flu tag and upstream of either (1) the truncated PSGL-1 lacking the apical domain, or (2) the CD43 repeat elements and transmembrane domain. Cells expressing the resulting chimeras were tested for their ability to bind to immobilized P-selectin (FIG. 9A). Conversion of the tyrosines to phenylalanines resulted in a loss of binding activity to P-selectin. Replacement of the threonine residues with alanine diminished binding, but did not abolish it entirely. Expression of the flu tag or sLe$^x$ epitope was not affected in these cells. Binding mediated by the apical 20 residues was, like that of native PSGL-1, dependent on the presence of calcium. These data indicate that sulfation of tyrosines at positions 46, 48, and 51 is required for P-selectin binding activity. E-selectin binding was unaffected under the same condition. In addition, these data indicate that the threonines at positions 44 and 57 are required. These threonine residues can serve as sites for O-linked glycan addition. These experiments, in conjunction with our experiments showing that FTVII expression is necessary for P-selectin binding, provide evidence that P-selectin binding requires sLe$^x$ at threonines 44 and 57. In sum, the above-described experiments demonstrate that amino acids 38-57, containing three residues for sulfation and two residues for sLe$^x$ addition, are sufficient to confer P-selectin binding activity.

Residues within the Amino-Terminal 20 Amino Acids are Sulfated on Tyrosine

Figure 12A:
FIG. 12A is a schematic diagram of immunoglobulin fusion proteins consisting of either intact PSGL-1 or 20 residue peptides joined to the hinge, CH2, and CH3 domains of human IgG1 (SEQ ID NOS:1, 4-7, and 9). Construct Y/F-hIgG bears SEQ ID NO:5; construct T/AhIgG bears SEQ ID NO:6; construct Y/F-T/A-hIgG bears SEQ ID NO:7.
Figure 12B:
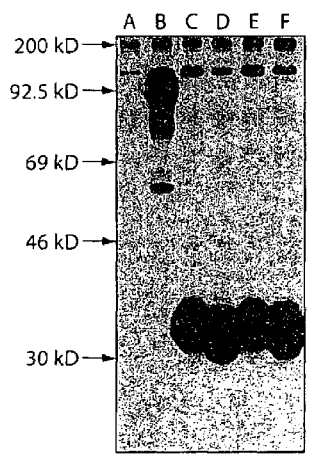
FIG. 12B is a photograph of an 8% polyacrylamide gel used to assess incorporation of [$^{35}$S]cysteine and methionine by the fusion proteins shown in FIG. 12A following transfection into COS cells. Lane A, supernatant of cells transfected with CDM8 control. Lane B, supernatant of cells transfected with PSGL-1-immunoglobulin fusion protein. Lane C, supernatant of cells transfected with WT-hIgG. Lane D, supernatant of cells transfected with Y/F-hIgG. Lane E, supernatant of cells transfected with T/A-hIgG. Lane F, supernatant of cells transfected with Y/F-T/A-hIgG.
Figure 12C:
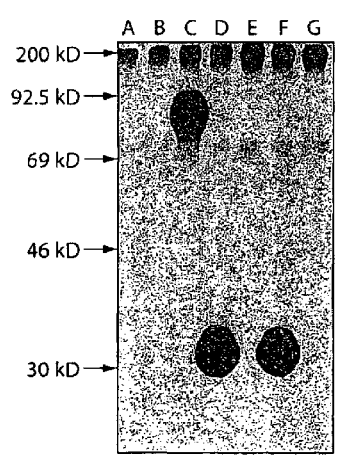
FIG. 12C is a photograph of an 8% polyacrylamide gel used to assess incorporation of [$^{35}$S]sulfate by the fusion proteins shown in FIG. 12A following transfection of COS cells. In addition, a control fusion protein bearing no amino-terminal addition was included (Lane B). Lanes C through G correspond to Lanes B through F in FIG. 12B.

To determine whether the amino-terminal segment was capable of being sulfated in vivo, we created fusion proteins consisting of the native or mutant peptide sequences joined to human immunoglobulin G1 (IgG1) (FIG. 12A). The resulting fusion proteins were expressed in COS cells, and their ability to assimilate inorganic sulfate was assessed (FIG. 12B). Immunoglobulin chimeras bearing the native peptide sequences were capable of incorporating sulfate, whereas those bearing phenylalanine substituted for tyrosine were not (FIG. 12C). Replacement of threonine with alanine had no effect on sulfate incorporation (FIG. 12C).

Figure 13:
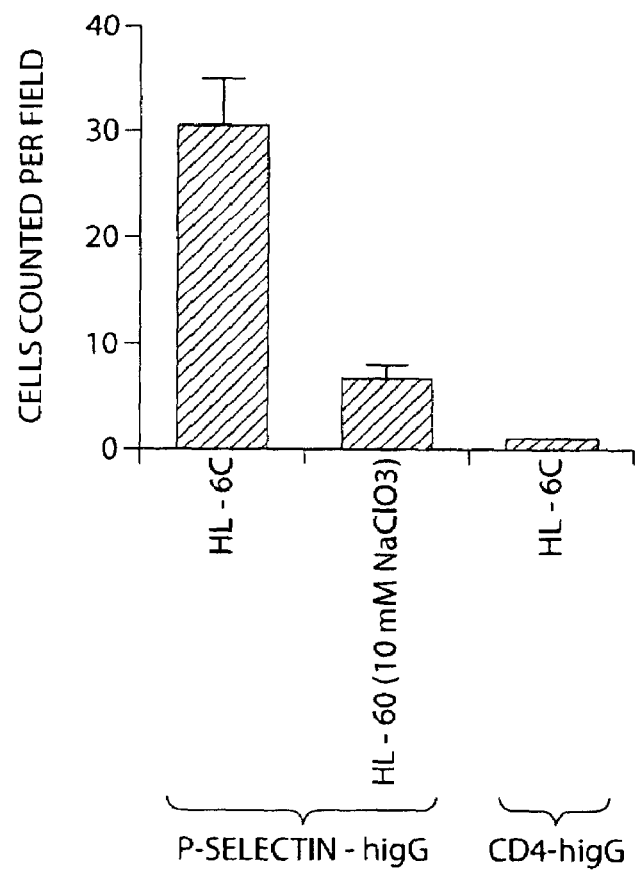
FIG. 13 is a bar graph of interacting HL-60 cells per video-captured field. The cells were infused into a parallel plate flow chamber precoated with either P-selectin-immunoglobulin chimera or a CD4-immunglobulin chimera control. The cells were subjected to a shear stress of 0.75 dynes/cm$^2$. Each bar represents the average number of cells (±SEM) per field from eight frames taken at 15 second intervals. Cells rolling or flowing appear as streaks on the video image. The bars represent, from left to right: HL-60 cells rolling or flowing over P-selectin-immunoglobin chimera, HL-60 cells pretreated in a sulfate-free medium with 10 mM sodium chlorate, and HL-60 cells flowing over CD4-immunoglobulin chimera.

Inhibitors of Sulfation Block HL-60 Rolling on P-Selectin-Immunoglobulin Chimeras To explore whether inhibition of sulfation would compromise a physiologically relevant adhesion, we subjected HL-60 cells to growth in medium containing chlorate and examined the ability of the resulting cells to attach and roll on coverslips coated with P-selectin-immunoglobulin chimeras under conditions of defined fluid shear stress (Lawrence et al., Blood, 75:227-237, 1990). HL-60 cells were capable of attaching to and rolling upon coverslips precoated with P-selectin-immunoglobulin chimeras, whereas no such interaction was observed with coverslips coated with a CD4 immunoglobulin chimera (FIG. 13). Growth of HL-60 cells in chlorate dramatically reduced the frequency of cell interaction with the substrate (FIG. 13).

A Preferred Synthetic P-Selectin Ligand

Figure 14:
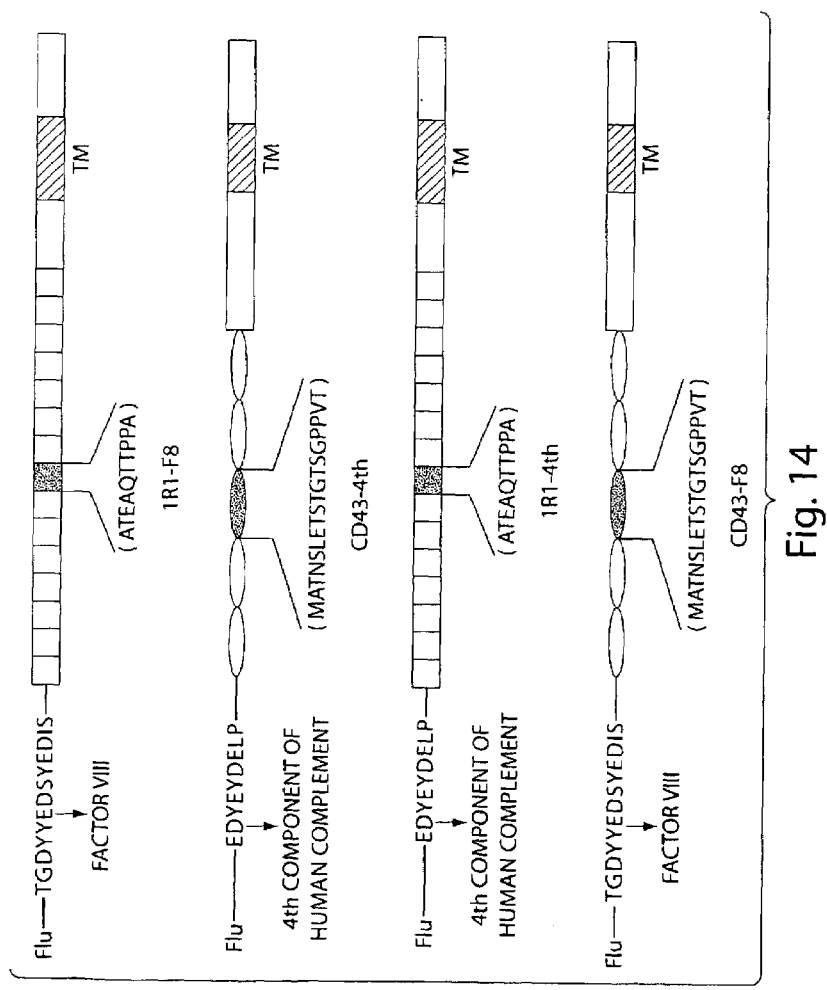
FIG. 14 is a schematic representation of putative synthetic P-selectin ligand constructs. Oligonucleotides encoding the tyrosine sulfation sites of either coagulation Factor VIII ("Factor VIII" or "F8") (SEQ ID NO:13) the fourth component of human complement ("4$^{th}$ Component of Human Complement" or "4$^{th}$") (SEQ ID NO:16) were inserted between a flu hemagglutinin tag ("Flu") and the amino-terminus of a sequence containing either PSGL-1 (the "1R1" construct) or CD43 (the "CD43" construct). The PSGL-1 repeat sequences (SEQ ID NO: 1) and the CD43 repeat sequences (SEQ ID NO: 2) are indicated, and the transmembrane domains (TM) are shown as hatched boxes.
Figure 15:
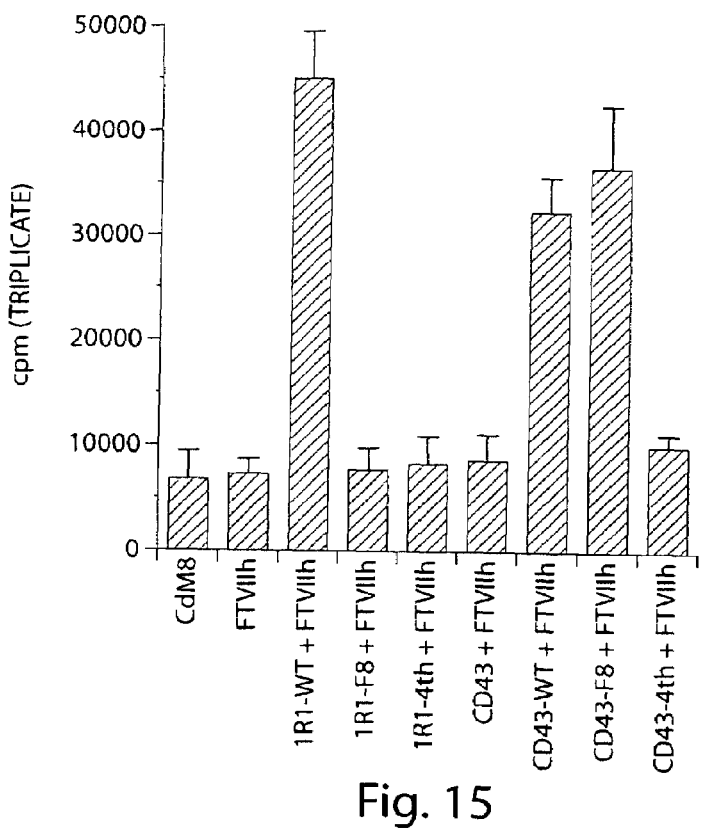
FIG. 15 is a histogram representing P-selectin binding activity of transfected COS cells expressing the chimeras of FIG. 14 or control proteins of FIG. 2A or 4A.

Candidate synthetic P-selectin ligands were constructed as described above. These ligands, which are depicted in FIG. 14, contained a tyrosine sulfation site from either coagulation Factor VIII or the fourth component of human complement linked to the repeat sequences of either PSGL-1 or human CD43. The human CD43 construct included no sequences derived from PSGL-1.

Expression plasmids encoding these putative ligands were each transfected into COS cells with a second expression plasmid encoding human fucosyltransferase VII (FTVIIh) (generally as described above). Cell surface expression of recombinant ligands was documented by cytometry using an anti-HA monoclonal antibody which recognized the flu tag sequence, and expression of the sialyl-Le$^x$ epitope was confirmed with an anti-sialyl-Le$^x$ monoclonal antibody (also as described above). In static binding assays, transfected COS cells expressing FTVIIh and the synthetic ligand, Factor VIII-CD43 (CD43-F8), bound to plastic coated with P-selectin Ig fusion protein (described above) approximately as well as did COS cells expressing the PSGL-1 tyrosine sulfation site grafted onto the repeat elements of PSGL-1 ("1R1-WT").

Antibodies and Antibody Fusion Proteins Bearing Sialyl-Le$^x$ and Sulfated Determinants In one embodiment, the invention features an antibody bearing sialyl-Le$^x$ and sulfated determinants. Such an antibody may be created by introducing sulfation sites (i.e., a tyrosine in an acidic context) into an existing antibody molecule in the vicinity of an introduced or existing sialyl-Le$^x$ addition site (for example, by standard site-directed mutagenesis). Alternatively, appropriate sialyl-Le$^x$ and/or sulfation sites may be added by appending any P-selectin ligand sequence (for example, any P-selectin ligand domain described herein) to a naturally-occurring antibody sequence (for example, IgG or IgM) by standard recombinant DNA techniques to produce a P-selectin ligand-antibody fusion protein. Preferably, the P-selectin ligand sequence is appended to the amino-terminus of the antibody molecule. Such antibodies are useful for disrupting undesirable interactions between cells or proteins, or, generally, for disrupting any interaction between two molecules, one of which bears a determinant carried by the antibody. Because these determinants normally act to facilitate interactions involving E-selectin and P-selectin (e.g., interactions between neutrophils and endothelial cells lining the blood vessel walls), the ability to disrupt such interactions provides many therapeutic applications, for example, in minimizing inflammation and decreasing extravasation-dependent organ damage and/or clotting.

In addition, if desired, one or more sialyl-Le$^x$ moieties which mask the CH2 portion of the immunoglobulin molecule and thus inhibit complement fixation and $F_c$ receptor binding may also be incorporated into the antibody sequence. Because the carbohydrate moieties block the immunoglobulin domain which triggers complement fixation and $F_c$ receptor binding, such antibodies do not elicit the undesirable side effects (i.e., those resulting from complement fixation and $F_c$ receptor binding) frequently associated with antibody-based therapies. Preferably, the carbohydrate groups serve not only to inhibit undesirable complement fixation and $F_c$ receptor binding, but also perform the function of competitively inhibiting an E-selectin and/or P-selectin mediated intracellular interaction.

To inhibit complement fixation and $F_c$ receptor binding, sialyl-Le$^x$ determinants may be added to the antibody molecule at any appropriate site. N-linked glycan addition sites are well known to be: N X S/T (where N is asparagine, S is serine, T is threonine, and X is any amino acid except proline). Accordingly, an exemplary molecule may be designed that includes several such sites for attachment of sialyl-Le$^x$ side chains. Inspection of the IgG1 sequence (FIG. 10) reveals at least five sites at which N-linked glycan addition sites may be introduced into the molecule in advantageous locations, where complement fixing and $F_c$ receptor binding ability will be impaired by the process. These sites include amino acid residues 274, 287, 295, 322, and 335. Although these are preferred sites of N-linked glycan addition, they are not the only candidates; other useful sites may be identified and incorporated into the IgG1 sequence using, as guidance, the following criteria: (1) the sites are, preferably, located in the CH2 region of the immunoglobulin molecule, i.e., in the portion of the molecule responsible for complement fixation and $F_c$ receptor binding; (2) the sites are located in regions of the sequence, predicted by their hydrophilic nature, to be present on the outside of the immunoglobulin molecule and therefore accessible to the enzymes responsible for attachment of carbohydrate side chains; (3) the sites are located in a region which is minimally disruptive to the primary amino acid sequence and, thus, the predicted secondary amino acid structure. For example, a naturally-occurring site which differs from an N-linked glycan addition site by a single amino acid would be preferable to a site requiring two alterations in the amino acid sequence. Moreover, it is preferable to create an N-linked glycan addition site by substituting amino acids of similar charge or polarity (e.g., substitution of one uncharged amino acid for another). One or more N-linked glycan addition site substitutions may be engineered into a particular IgG1-encoding sequence; such sequences (i.e., those which encode an antibody molecule to which sialyl-Le$^x$ moieties are attached) are termed IgG1-sialyl-Le$^x$ or IgG1-Le$^x$.

The introduction of additional glycosylation sites at amino acids #274, #287, and #322 within the CH2 domain created a molecule that was unrecognized by F$_c$ receptor or complement using assays that are standard in the art; exemplary complement fixation assays include Weir et al., *Handbook of Experimental Immunology*, Blackwell, Oxford; and Coligan et al. *Current Protocols In Immunology*, Wiley Interscience, 1995.

A particular IgG1 molecule bearing sialyl-Le$^x$ moieties is produced as follows. The IgG1 gene is publically available, and its sequence is shown in FIG. 10. The gene is mutagenized by standard methods of in vitro site-directed mutagenesis in order to introduce one or more N-linked glycan addition sites (e.g., those described above and shown above the naturally-occurring sequence in FIG. 10). The gene is then inserted into a vector designed to express the protein in a eukaryotic cell (see, e.g., those vectors described in Gillies et al., U.S. Pat. No. 4,663,281, hereby incorporated by reference). The eukaryotic host cell is preferably a mammalian cell (e.g., a CHO or lec11 cell), and the expression vector containing the mutated IgG1-Le$^x$-encoding sequence is introduced into the host cell by transient or stable transfection using standard techniques. Such host cells are also transfected (transiently or stably) with a vector capable of expressing an α(1,3)fucosyltransferase capable of attaching the sialyl-Le$^x$ groups to the antibody molecule at the glycosylation sites. The α(1,3)fucosyltransferase gene may be expressed from a vector distinct from that encoding IgG1-Le$^x$, or both genes may be carried on, and expressed from, a common vector. Mammalian cells are particularly useful hosts for the synthesis of IgG1-Le$^x$ because they provide all required precursors for sialyl-Le$^x$ production.

To produce the sialyl-Le$^x$-modified and sulfated antibodies of the invention, the gene encoding the antibody sequence is preferably expressed in a cell which also expresses an α(1,3) fucosyltransferase that exclusively catalyzes α(1,3)fucose linkages; such an enzyme is described in Walz et al., Science 250:1132-1135 (1990) and in Seed, U.S. Ser. No. 08/483,151, entitled "Fucosyltransferase Genes and Uses Thereof," filed Jun. 7, 1995 (hereby incorporated by reference). Less preferably, the α(1,3)fucosyltransferase cDNA described in Lowe et al. (Cell 63:475, 1990) may be utilized. This fucosyltransferase recognizes a sialylated precursor molecule and adds either an α(1,3)- or an α(1,4)-linked fucose moiety to N-acetylglucosamine side chains. The sialyl-Le$^x$ determinant is characterized by an α(1,3)-linkage, and, as such, the α(1,3)fucosyltransferase enzyme of Lowe (supra) produces both the desired sialyl-Le$^x$-modified molecules and products bearing α(1,4)-linked fucose which, although not active in binding to P-selectin and E-selectin, do not interfere with the action of the sialyl-Le$^x$-modified molecules nor produce other undesirable side effects.

Host cells expressing α(1,3)fucosyltransferase and the antibody to be modified are grown by standard methods, and the antibody is purified from a cell lysate based on its affinity for a Protein A column or any other standard technique of antibody isolation and purification.

α$_1$-Acid Glycoprotein-Antibody Fusion Proteins Bearing Sialyl-Le$^x$ and Sulfated Determinants As discussed herein, antibody fusion proteins modified by sulfation and sialyl-Le$^x$ addition have important therapeutic and diagnostic uses. Previous work has demonstrated that large amounts of antibody fusion proteins may be generated and secreted transiently from transfected mammalian cells (for example, COS cells). In general, to produce an AGP antibody fusion protein according to the invention, DNA encoding an AGP and a P-selectin ligand domain are fused in-frame to human IgG domains (for example, constant domains) by standard techniques, and the fusion protein is expressed, also by standard techniques. The antibody portion of the molecule facilitates fusion protein purification and also prolongs the plasma half-life of otherwise short-lived polypeptides or polypeptide domains. Preferably, antibody fusion proteins are A expressed according to the methods disclosed in Seed et al., U.S. Ser. No. 08/483,151 entitled "Fucosyltransferase Genes and Uses Thereof," filed Jun. 7, 1995 (which is hereby incorporated by reference), e.g., using IgG or IgM antibodies or portions thereof (see also Zettlemeisl et al., DNA Cell Biol. 9:347 (1990) for IgM fusion proteins).

Recombinant plasmids expressing particular AGP-antibody fusion proteins (e.g., AGP-Hinge-CH2-CH3 and AGP-CH2-CH3 proteins) have been constructed as follows. A cDNA encoding the acute phase α$_1$-AGP gene was cloned from a human liver cDNA library by polymerase chain reaction (PCR) using oligonucleotide primers corresponding to the 5' and 3' coding regions of α$_1$-AGP (Board et al., Gene 44:127, 1986) according to standard techniques. The 5' AGP primer was designed to contain a HindIII restriction site and the 3' primer was designed to contain a BamHI restriction site rather than the AGP stop codon. The PCR-amplified product was digested with HindIII/BamHI and cloned into a HindIII/BamHI-cut plasmid expression cassette (see Aruffo et al., Cell, 61:1303, 1990) containing constant domains of human IgG1 (i.e., Hinge-CH2-CH3 or CH2-CH3). A nucleotide sequence and amino acid sequence of this AGP-IgG fusion protein are shown in FIG. 11A and FIG. 11B, respectively.

To create a molecule that blocks P-selectin-mediated interactions, sites for sulfation and, if necessary, sialyl-Le$^x$ addition are introduced into the antibody fusion protein sequence (for example, the antibody fusion proteins described above). Such sites may be incorporated into an existing fusion molecule, for example, by introducing one or more sulfation sites (i.e., a tyrosine in an acidic context) in the vicinity of an introduced or existing sialyl-Le$^x$ addition site (for example, by standard techniques of site-directed mutagenesis), or a P-selectin ligand sequence (for example, any of the P-selectin ligand sequences described herein) may be appended to the antibody fusion protein sequence using standard techniques of recombinant DNA technology.

The P-selectin-AGP-antibody fusion genes are then introduced into expression plasmids, and the plasmids are transfected into any appropriate fucosyltransferase-expressing cell for the production of soluble antibody fusion proteins.

To prepare an antibody fusion protein capable of inhibiting complement fixation and F$_c$ receptor binding, additional sialyl-Le$^x$ consensus glycosylation sites (N-X-T/S) may be introduced into the CH2 domain of human IgG1 as described above.

Based on this construction strategy, any number of recombinant P-selectin-AGP-antibody fusion proteins may be designed having long plasma half-lives and the ability to inhibit undesirable cell-cell interactions (for example, the interactions between leukocytes and selectin-bearing cells). To generate molecules with heightened inhibitory potency, candidate molecules are designed and screened using the assays described above. In one particular example, molecules may be screened for their ability to incorporate sialyl-Le$^x$ and sulfated determinants and block the binding of neutrophils to activated endothelial cells; such molecules find use in the inhibition of selectin-dependent inflammatory reactions and tissue injury inflicted by invading leukocytes.

Molecules Capable of Interfering with P-Selectin-Mediated and E-Selectin-Mediated Interactions Because both P-selectin- and E-selectin-mediated intracellular interactions are involved in inflammation and because the crucial determinants involved in those interactions have now been identified, it is possible to design a single molecule capable of interfering with both types of deleterious interactions. In particular, molecules (for example, proteins) may be constructed that include both a P-selectin ligand domain (i.e., a domain bearing sialyl-Le$^x$ and sulfated moieties) and an E-selectin ligand domain (i.e., a domain bearing a sialyl-Le$^x$ moiety). Such a molecule may be constructed by combining domains, for example, by appending a P-selectin ligand domain to a sialylated molecule (for example, a sialylated antibody or antibody fusion protein described herein). Alternatively, appropriate sialyl-Le$^x$ and/or sulfation sites may be introduced into an existing sequence, for example, by site directed mutagenesis.

Glycosylation or sulfation of an engineered molecule may be tested, for example, as described herein and in Walz et al., Science 250:1132-1135 (1990). The ability of a sialyl-Le$^x$-modified and/or sulfated molecule to interfere with intracellular interactions may also be tested as described in Walz et al., supra, or by any standard technique, for example, by assaying the ability of increasing concentrations of the determinant-bearing molecule to inhibit adherence of T lymphocytes or myeloid cells to immobilized P-selectin and/or E-selectin.

Use

For administering a protein or organic molecule of the invention to a patient, the pharmaceutically-pure protein or molecule is suspended in an acceptable carrier, e.g., physiological saline, and is delivered to the patient by any appropriate route (for example, intravenously) in a single dose or in multiple doses. Optimally, a sufficient quantity of the therapeutic is provided to saturate all P-selectin and, for a dual function molecule, all E-selectin binding sites on an endothelial cell. Typically, this may be achieved with doses of 0.1 mg/kg or greater. The preferred dosage is in the range of 0.1-2.0 mg/kg.

The sialyl-Le$^x$-modified and sulfated molecules and proteins of the invention (for example, the modified antibodies and antibody fusion proteins described herein) may be used, in one example, for the treatment of extravasation-dependent organ damage and/or clotting. In particular, because P-selectin mediates the attachment of neutrophils overlying sites of inflammation or tissue damage or proximate to thrombus formation, the molecules and proteins of the invention provide useful therapeutics for blocking such interactions. For example, P-selectin likely mediates the migration of neutrophils into the lung following adult respiratory distress syndrome and into the heart following ischemic myocardial injury (i.e., infarction), and may play a role in glomerular damage to the kidneys under certain conditions. Accordingly, a sialyl-Le$^x$-modified and sulfated molecule or protein of the invention may be administered to a patient suffering from such a disease or condition. Such treatment attenuates extravasation-dependent damage by competitively inhibiting the interaction between the invading neutrophils and the endothelial cells of the blood vessel or organ. The compounds of the invention, particularly, P-selectin ligand-AGP fusion proteins and P-selectin ligand-AGP-antibody fusion proteins may also be used, as described above, for the treatment of septic shock or septicemia.

In addition, antibodies or antibody fusion proteins according to the invention may be used in conventional techniques of antibody-based therapies or in vivo diagnostics, taking advantage of the antibody's specificity to target therapeutic or diagnostic sites. In one particular example, the P-selectin ligand domain of an antibody fusion protein according to the invention targets that protein to a site of inflammation and provides both a therapeutic (useful for blocking deleterious P-selectin-mediated intracellular interactions) and a diagnostic (useful for tagging the site of inflammation). Again, attached sialyl-Le$^x$ determinants may be used to mask the CH2 domain of the antibody and block the undesirable effects of complement fixation and $F_c$ receptor binding.

OTHER EMBODIMENTS

Other embodiments are within the claims. For example, for the purpose of blocking interactions between cells or proteins, any other appropriate carrier molecule to which a sialyl-Le$^x$ and a sulfated determinant may be attached may be utilized in the invention. Generally, proteins are preferred because of their relatively long half-lives in serum. One class of carrier proteins are serum proteins such as albumin (e.g., bovine serum albumin or human serum albumin), transferrin, or α-2 macroglobulin. The carrier proteins may contain endogenous sulfation and glycan addition sites in addition to which sites are introduced into the DNA sequence of the carrier protein (as described above) by, for example, site-directed mutagenesis. The carrier molecule, less preferably, may be a lipid. In one example, the lipid, with one or more attached sialyl-Le$^x$ and sulfated determinants is delivered as a liposome to a target cell wall (e.g., an endothelial cell wall). The liposome may block a cell or protein interaction or may be used to deliver a drug to its appropriate site of action.

Production of carrier molecules bearing sialyl-Le$^x$ and sulfated determinants may be carried out in a cell, preferably, a eukaryotic cell other than yeast. Mammalian cells, e.g., mammalian cell lines, provide particularly suitable hosts. These cells generally synthesize the necessary precursor molecules and produce or can be engineered to produce the enzymes responsible for sulfation and carbohydrate attachment. For the attachment of sialyl-Le$^x$ determinants, mammalian cell lines such as CHO and lec11 are particularly suitable. Alternatively, either or both of the sialyl-Le$^x$ and sulfated determinants may be attached to a carrier molecule in vitro, i.e., extracellularly. In one example, α(1,3)fucosyltransferase would be bound to a solid support (e.g., a column) and a sulfated carrier molecule passed over the bound fucosyltransferase enzyme, under conditions which facilitate attachment of sialyl-Le$^x$ groups to their appropriate site(s) on the carrier molecule.

The invention also encompasses the use of sulfated and sialyl-Le$^x$-modified AGP-antibody fusion proteins for protecting against, inhibiting, or treating a shock-inducing event, the clinical manifestations of shock, or both which are caused by microbial factors (e.g., lipopolysaccharides (LPS)), microbial toxins (e.g., toxic shock enterotoxins), host mediators (e.g., cytokines), or anti-tumor therapies (e.g., administration of tumor necrosis factor (TNF) or interleukin-1 (IL-1)), or any combination thereof. For example, such an antibody fusion protein can be administered to a human patient to alleviate the effects of septic shock induced by microbial LPS. The ability of an antibody fusion protein to protect against, treat, or inhibit the effects of shock (e.g., septicemia or toxic shock syndrome) is evaluated according to standard methods known in the art (e.g., those described in Libert et al. (1994) J. Exp. Med. 180: 1571-1575).

All publications, patents, and patent applications mentioned in this specification are herein incorporated by reference to the same extent as if each individual publication, patent, and patent application was specifically and individually indicated to be incorporated by reference.

The invention claimed is:

1. A purified nucleic acid encoding a polypeptide that is a synthetic P-selectin ligand, wherein said polypeptide contains an N-linked sialyl Le$^x$ addition site and a tyrosine sulfation site, and wherein at least one of the sites is located at an amino acid position in said polypeptide which is different from its position in a naturally-occurring P-selectin ligand.

2. The purified nucleic acid of claim 1, wherein said nucleic add further encodes an antibody or antibody fusion protein.

3. A vector comprising the nucleic acid of claim 1.

4. A cell comprising the purified nucleic acid of claim 1.

5. The purified nucleic acid of claim 1, wherein said tyrosine sulfation site consists of the Factor VIII tyrosine sulfation sequence set forth in SEQ ID NO: 15.

6. The purified nucleic acid of claim 1, wherein said polypeptide comprises Ile135 through Ser225 of the CD43 precursor sequence (SEQ ID NO: 17).

* * * * *

SEQUENCE LISTING

```
<160> NUMBER OF SEQ ID NOS: 17

<210> SEQ ID NO 1
<211> LENGTH: 10
<212> TYPE: PRT
<213> ORGANISM: Homo sapiens

<400> SEQUENCE: 1

Ala Thr Glu Ala Gln Thr Thr Pro Pro Ala
 1               5                  10

<210> SEQ ID NO 2
<211> LENGTH: 18
<212> TYPE: PRT
<213> ORGANISM: Homo sapiens

<400> SEQUENCE: 2

Met Ala Thr Asn Ser Leu Glu Thr Ser Thr Gly Thr Ser Gly Pro Pro
 1               5                  10                  15

Val Thr

<210> SEQ ID NO 3
<211> LENGTH: 42
<212> TYPE: PRT
<213> ORGANISM: Homo sapiens

<400> SEQUENCE: 3

Gln Leu Trp Asp Thr Trp Ala Asp Glu Ala Glu Lys Ala Leu Gly Pro
 1               5                  10                  15

Leu Leu Ala Arg Asp Arg Arg Gln Ala Thr Glu Tyr Glu Tyr Leu Asp
                20                  25                  30

Tyr Asp Phe Leu Pro Glu Thr Glu Pro Pro
                35                  40

<210> SEQ ID NO 4
<211> LENGTH: 20
<212> TYPE: PRT
<213> ORGANISM: Homo sapiens

<400> SEQUENCE: 4

Arg Asp Arg Arg Gln Ala Thr Glu Tyr Glu Tyr Leu Asp Tyr Asp Phe
 1               5                  10                  15

Leu Pro Glu Thr
                20

<210> SEQ ID NO 5
<211> LENGTH: 20
<212> TYPE: PRT
<213> ORGANISM: Homo sapiens

<400> SEQUENCE: 5
```

Arg Asp Arg Arg Gln Ala Thr Glu Phe Glu Phe Leu Asp Phe Asp Phe
1               5                   10                  15

Leu Pro Glu Thr
            20

<210> SEQ ID NO 6
<211> LENGTH: 20
<212> TYPE: PRT
<213> ORGANISM: Homo sapiens

<400> SEQUENCE: 6

Arg Asp Arg Arg Gln Ala Ala Glu Tyr Glu Tyr Leu Asp Tyr Asp Phe
1               5                   10                  15

Leu Pro Glu Ala
            20

<210> SEQ ID NO 7
<211> LENGTH: 20
<212> TYPE: PRT
<213> ORGANISM: Homo sapiens

<400> SEQUENCE: 7

Arg Asp Arg Arg Gln Ala Ala Glu Phe Glu Phe Leu Asp Phe Asp Phe
1               5                   10                  15

Leu Pro Glu Ala
            20

<210> SEQ ID NO 8
<211> LENGTH: 2287
<212> TYPE: DNA
<213> ORGANISM: Homo sapiens

<400> SEQUENCE: 8

| | | | | | |
|---|---|---|---|---|---|
| aagcttacca | ccatggactg | gacctggagg | ttcctcttct | tgtggtggc | agcagctaca | 60 |
| ggtgtccagt | cccaggtgca | gctggtgcag | tctggggctg | aggtgaagaa | gcctgggtcc | 120 |
| tcggtgaagg | tctcctgcaa | ggcttctgga | ggcaccttca | gcagctatgc | tatcagctgg | 180 |
| gtgcgacagg | cccctggaca | agggcttgag | tggatgggag | ggatcatccc | tatctttggt | 240 |
| acagcaaact | acgcacagaa | gttccagggc | agagtcacga | ttaccgcgga | cgaatccacg | 300 |
| agcacagcct | acatggagct | gagcagcctg | agatctgagg | acacggccgt | gtattactgt | 360 |
| gcgagagata | tggagcgta | ttgtagtggt | ggtagctgct | actcgggctg | gttcgacccc | 420 |
| tggggccagg | gaaccctggt | caccgtctct | tcaggtgagt | actgaattct | agctttctgg | 480 |
| ggcaggccag | gcctgacctt | ggctttgggg | cagggagggg | gctaaggtga | ggcaggtggc | 540 |
| gccagcaggt | gcacacccaa | tgcccatgag | cccagacact | ggacgctgaa | cctcgcggac | 600 |
| agttaagaac | ccaggggcct | ctgcgcctgg | gcccagctct | gtcccacacc | gcggtcacat | 660 |
| ggcaccacct | ctcttgcagc | ctccaccaag | ggcccatcgg | tcttccccct | ggcaccctcc | 720 |
| tccaagagca | cctctggggg | cacagcggcc | ctgggctgcc | tggtcaagga | ctacttcccc | 780 |
| gaaccggtga | cggtgtcgtg | gaactcaggc | gccctgacca | gcggcgtgca | cacctteccg | 840 |
| gctgtcctac | agtcctcagg | actctactcc | ctcagcagcg | tggtgaccgt | gccctccagc | 900 |
| agcttgggca | cccagaccta | catctgcaac | gtgaatcaca | agcccagcaa | caccaaggtg | 960 |
| gacaagaaag | ttggtgagag | gccagcacag | ggagggaggg | tgtctgctgg | aagcaggctc | 1020 |
| agcgctcctg | cctggacgca | tcccggctat | gcagccccag | tccagggcag | caaggcaggc | 1080 |
| cccgtctgcc | tcttcacccg | gaggcctctg | ccgccccact | catgctcagg | gagagggtct | 1140 |

```
tctggctttt tcccaggctc tgggcaggca caggctaggt gcccctaacc caggccctgc    1200
acacaaaggg gcaggtgctg ggctcagacc tgccaagagc catatccggg aggaccctgc    1260
ccctgaccta agcccacccc aaaggccaaa ctctccactc cctcagctcg gacaccttct    1320
ctcctcccag attccagtaa ctcccaatct tctctctgca gagcccaaat cttgtgacaa    1380
aactcacaca tgcccaccgt gcccaggtaa gccagcccag gcctcgccct ccagctcaag    1440
gcgggacagg tgccctagag tagcctgcat ccagggacag gccccagccg ggtgctgaca    1500
cgtccacctc catctcttcc tcagcacctg aactcctggg gggaccgtca gtcttcctct    1560
tccccccaaa acccaaggac accctcatga tctcccggac ccctgaggtc acatgcgtgg    1620
tggtggacgt gagccacgaa gaccctgagg tcaagttcaa ctggtacgtg gacggcgtgg    1680
aggtgcataa tgccaagaca aagccgcggg aggagcagta caacagcacg taccgggtgg    1740
tcagcgtcct caccgtcctg caccaggact ggctgaatgg caaggagtac aagtgcaagg    1800
tctccaacaa agccctccca gcccccatcg agaaaaccat ctccaaagcc aaaggtggga    1860
cccgtggggt gcgagggcca catggacaga ggccggctcg gcccaccctc tgccctgaga    1920
gtgaccgctg taccaacctc tgtcctacag ggcagccccg agaaccacag gtgtacaccc    1980
tgcccccatc ccgggatgag ctgaccaaga accaggtcag cctgacctgc ctggtcaaag    2040
gcttctatcc cagcgacatc gccgtggagt gggagagcaa tgggcagccg gagaacaact    2100
acaagaccac gcctcccgtg ctggactccg acggctcctt cttcctctac agcaagctca    2160
ccgtggacaa gagcaggtgg cagcagggga acgtcttctc atgctccgtg atgcatgagg    2220
ctctgcacaa ccactacacg cagaagagcc tctccctgtc tccgggtaaa tgagtgcgac    2280
ggccggc                                                             2287
```

<210> SEQ ID NO 9
<211> LENGTH: 442
<212> TYPE: PRT
<213> ORGANISM: Homo sapiens

<400> SEQUENCE: 9

```
Lys Leu Thr Thr Met Asp Trp Thr Trp Arg Phe Leu Phe Val Val
 1               5                  10                  15

Ala Ala Ala Thr Gly Val Gln Ser Gln Val Gln Leu Val Gln Ser Gly
            20                  25                  30

Ala Glu Val Lys Lys Pro Gly Ser Ser Val Lys Val Ser Cys Lys Ala
        35                  40                  45

Ser Gly Gly Thr Phe Ser Ser Tyr Ala Ile Ser Trp Val Arg Gln Ala
    50                  55                  60

Pro Gly Gln Gly Leu Glu Trp Met Gly Gly Ile Ile Pro Ile Phe Gly
65                  70                  75                  80

Thr Ala Asn Tyr Ala Gln Lys Phe Gln Gly Arg Val Thr Ile Thr Ala
                85                  90                  95

Asp Glu Ser Thr Ala Arg Asp Asn Gly Ala Tyr Cys Ser Gly Gly Ser
            100                 105                 110

Cys Tyr Ser Gly Trp Phe Asp Pro Trp Gly Gln Gly Thr Leu Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160
```

```
Lys Asp Tyr Phe Pro Glu Pro Val Thr Val Ser Trp Asn Ser Gly Ala
                165                 170                 175
Leu Thr Ser Gly Val His Thr Phe Pro Ala Val Leu Gln Ser Ser Gly
            180                 185                 190
Leu Tyr Ser Leu Ser Ser Val Val Thr Val Pro Ser Ser Ser Asp Lys
        195                 200                 205
Lys Val Glu Pro Lys Ser Cys Asp Lys Thr His Thr Cys Pro Pro Cys
    210                 215                 220
Pro Ala Pro Glu Leu Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
        275                 280                 285
Glu Gln Tyr Asn Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Asp Glu
            340                 345                 350
Leu Thr Lys Asn Gln Val Ser Leu Thr Cys Leu Val Lys Gly Phe Tyr
        355                 360                 365
Pro Ser Asp Ile Ala Val Glu Trp Glu Ser Asn Gly Gln Pro Glu Asn
    370                 375                 380
Asn Tyr Lys Thr Thr Pro Pro Val Leu Asp Ser Asp Gly Ser Phe Phe
385                 390                 395                 400
Leu Tyr Ser Lys Leu Thr Val Asp Lys Ser Arg Trp Gln Gln Gly Asn
                405                 410                 415
Val Phe Ser Cys Ser Val Met His Glu Ala Leu His Asn His Tyr Thr
            420                 425                 430
Gln Lys Ser Leu Ser Leu Ser Pro Gly Lys
        435                 440

<210> SEQ ID NO 10
<211> LENGTH: 1894
<212> TYPE: DNA
<213> ORGANISM: Homo sapiens

<400> SEQUENCE: 10
atggcgctgt cctgggttct tacagtcctg agcctcctac ctctgctgga agcccagatc    60
ccattgtgtg ccaacctagt accggtgccc atcaccaacg ccaccctgga ccagatcact   120
ggcaagtggt tttatatcgc atcggccttt cgaaacgagg agtacaataa gtcggttcag   180
gagatccaag caaccttctt ttacttcacc cccaacaaga cagaggacac gatctttctc   240
agagagtacc agacccgaca ggaccagtgc atctataaca ccacctacct gaatgtccag   300
cgggaaaatg ggaccatctc agatacgtg ggaggccaag agcatttcgc tcacttgctg   360
atcctcaggg acaccaagac ctacatgctt gcttttgacg tgaacgatga aagaactgg   420 gggctgtctg tctatgctga caagccagag acgaccaagg agcaactggg agagttctac   480
gaagctctcg actgcttgcg cattcccaag tcagatgtcg tgtacaccga ttggaaaaag   540
```

```
gataagtgtg agccactgga gaagcagcac gagaaggaga ggaaacagga ggaggggggaa      600 tcggatcccg agggtgagta ctaagcttca gcgctcctgc ctggacgcat cccggctatg      660
cagccccagt ccagggcagc aaggcaggcc ccgtctgcct cttcacccgg agcctctgcc      720
cgccccactc atgctcaggg agagggtctt ctggcttttt cccaggctct gggcaggcac      780
aggctaggtg cccctaaccc aggccctgca cacaaagggg caggtgctgg gctcagacct      840
gccaagagcc atatccggga ggaccctgcc cctgacctaa gcccacccca aaggccaaac      900
tctccactcc ctcagctcgg acaccttctc tcctcccaga ttccagtaac tcccaatctt      960
ctctctgcag agcccaaatc ttgtgacaaa actcacacat gcccaccgtg cccaggtaag     1020
ccagcccagg cctcgccctc cagctcaagg cgggacaggt gccctagagt agcctgcatc     1080
cagggacagg ccccagccgg gtgctgacac gtccacctcc atctcttcct cagcacctga     1140
actcctgggg ggaccgtcag tcttcctctt ccccccaaaa cccaaggaca ccctcatgat     1200
ctcccggacc cctgaggtca catgcgtggt ggtggacgtg agccacgaag accctgaggt     1260
caagttcaac tggtacgtgg acggcgtgga ggtgcataat gccaagacaa agccgcggga     1320
ggagcagtac aacagcacgt accgggtggt cagcgtcctc accgtcctgc accaggactg     1380
gctgaatggc aaggagtaca agtgcaaggt ctccaacaaa gccctcccag cccccatcga     1440
gaaaaccatc tccaaagcca aggtgggacc cgtggggtg cgagggccac atggacagag     1500
gccggctcgg cccaccctct gccctgagag tgaccgctgt accaacctct gtcctacagg     1560
gcagccccga gaaccacagg tgtacaccct gcccccatcc cgggatgagc tgaccaagaa     1620
ccaggtcagc ctgacctgcc tggtcaaagg cttctatccc agcgacatcg ccgtggagtg     1680
ggagagcaat gggcagccgg agaacaacta caagaccacg cctcccgtgc tggactccga     1740
cggctccttc ttcctctaca gcaagctcac cgtggacaag agcaggtggc agcaggggaa     1800
cgtcttctca tgctccgtga tgcatgaggc tctgcacaac cactacacgc agaagagcct     1860
ctccctgtct ccgggtaaat gagtgcgacg gccg                                 1894
```

<210> SEQ ID NO 11
<211> LENGTH: 437
<212> TYPE: PRT
<213> ORGANISM: Homo sapiens

<400> SEQUENCE: 11

```
Met Ala Leu Ser Trp Val Leu Thr Val Leu Ser Leu Leu Pro Leu Leu
 1               5                  10                  15

Glu Ala Gln Ile Pro Leu Cys Ala Asn Leu Val Pro Val Pro Ile Thr
            20                  25                  30

Asn Ala Thr Leu Asp Gln Ile Thr Gly Lys Trp Phe Tyr Ile Ala Ser
        35                  40                  45

Ala Phe Arg Asn Glu Glu Tyr Asn Lys Ser Val Gln Glu Ile Gln Ala
    50                  55                  60

Thr Phe Phe Tyr Phe Thr Pro Asn Lys Thr Glu Asp Thr Ile Phe Leu
65                  70                  75                  80

Arg Glu Tyr Gln Thr Arg Gln Asp Gln Cys Ile Tyr Asn Thr Thr Tyr
                85                  90                  95

Leu Asn Val Gln Arg Glu Asn Gly Thr Ile Ser Arg Tyr Val Gly Gly
            100                 105                 110

Gln Glu His Phe Ala His Leu Leu Ile Leu Arg Asp Thr Lys Thr Tyr
        115                 120                 125
```

-continued

```
Met Leu Ala Phe Asp Val Asn Asp Glu Lys Asn Trp Gly Leu Ser Val
    130                 135                 140

Tyr Ala Asp Lys Pro Glu Thr Thr Lys Glu Gln Leu Gly Glu Phe Tyr
145                 150                 155                 160

Glu Ala Leu Asp Cys Leu Arg Ile Pro Lys Ser Asp Val Val Tyr Thr
                165                 170                 175

Asp Trp Lys Lys Asp Lys Cys Glu Pro Leu Glu Lys Gln His Glu Lys
            180                 185                 190

Glu Arg Lys Gln Glu Glu Gly Glu Ser Asp Pro Glu Gly Glu Pro Lys
        195                 200                 205

Ser Cys Asp Lys Thr His Thr Cys Pro Pro Cys Pro Ala Pro Glu Leu
    210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Asp Glu Leu Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys
        435
```

<210> SEQ ID NO 12
<211> LENGTH: 442
<212> TYPE: PRT
<213> ORGANISM: Homo sapiens

<400> SEQUENCE: 12

```
Lys Leu Thr Thr Met Asp Trp Thr Trp Arg Phe Leu Phe Val Val
1               5                   10                  15

Ala Ala Ala Thr Gly Val Gln Ser Gln Val Gln Leu Val Gln Ser Gly
            20                  25                  30

Ala Glu Val Lys Lys Pro Gly Ser Ser Val Lys Val Ser Cys Lys Ala
        35                  40                  45

Ser Gly Gly Thr Phe Ser Ser Tyr Ala Ile Ser Trp Val Arg Gln Ala
    50                  55                  60
```

```
Pro Gly Gln Gly Leu Glu Trp Met Gly Gly Ile Ile Pro Ile Phe Gly
 65                  70                  75                  80

Thr Ala Asn Tyr Ala Gln Lys Phe Gln Gly Arg Val Thr Ile Thr Ala
                 85                  90                  95

Asp Glu Ser Thr Ala Arg Asp Asn Gly Ala Tyr Cys Ser Gly Gly Ser
            100                 105                 110

Cys Tyr Ser Gly Trp Phe Asp Pro Trp Gly Gln Gly Thr Leu Val Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Asn Phe Ser Trp
            260                 265                 270

Tyr Val Asp Gly Val Glu Val His Asn Asn Lys Thr Lys Pro Arg Glu
        275                 280                 285

Glu Asn Tyr Ser Ser Thr Tyr Arg Val Val Ser Val Leu Thr Val Leu
    290                 295                 300

His Gln Asp Trp Leu Asn Gly Lys Glu Tyr Lys Cys Asn Val Ser Asn
305                 310                 315                 320

Lys Ala Leu Pro Ala Pro Ile Glu Lys Asn Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 13
<211> LENGTH: 42
<212> TYPE: PRT
<213> ORGANISM: Homo sapiens
```

-continued

<400> SEQUENCE: 13

Pro Glu Met Leu Arg Asn Ser Thr Asp Thr Thr Pro Leu Thr Gly Pro
1               5                   10                  15

Gly Thr Pro Glu Ser Thr Thr Val Glu Pro Ala Ala Arg Arg Ser Thr
            20                  25                  30

Gly Leu Asp Ala Gly Gly Ala Val Thr Glu
            35                  40

<210> SEQ ID NO 14
<211> LENGTH: 16
<212> TYPE: PRT
<213> ORGANISM: Homo sapiens

<400> SEQUENCE: 14

Leu Thr Thr Glu Leu Ala Asn Met Gly Asn Leu Ser Thr Asp Ser Ala
1               5                   10                  15

<210> SEQ ID NO 15
<211> LENGTH: 13
<212> TYPE: PRT
<213> ORGANISM: Homo sapiens

<400> SEQUENCE: 15

Thr Gly Asp Tyr Tyr Glu Asp Ser Tyr Glu Asp Ile Ser
1               5                   10

<210> SEQ ID NO 16
<211> LENGTH: 9
<212> TYPE: PRT
<213> ORGANISM: Homo sapiens

<400> SEQUENCE: 16

Glu Asp Tyr Glu Tyr Asp Glu Leu Pro
1               5

<210> SEQ ID NO 17
<211> LENGTH: 91
<212> TYPE: PRT
<213> ORGANISM: Homo sapiens

<400> SEQUENCE: 17

Ile Thr Thr Asn Ser Pro Glu Thr Ser Ser Arg Thr Ser Gly Ala Pro
1               5                   10                  15

Val Thr Thr Ala Ala Ser Ser Leu Glu Thr Ser Arg Gly Thr Ser Gly
            20                  25                  30

Pro Pro Leu Thr Met Ala Thr Val Ser Leu Glu Thr Ser Lys Gly Thr
            35                  40                  45

Ser Gly Pro Pro Val Thr Met Ala Thr Asp Ser Leu Glu Thr Ser Thr
        50                  55                  60

Gly Thr Thr Gly Pro Pro Val Thr Met Thr Thr Gly Ser Leu Glu Pro
65                  70                  75                  80

Ser Ser Gly Ala Ser Gly Pro Gln Val Ser Ser
                85                  90